United States Patent
Iyer et al.

(10) Patent No.: US 9,061,161 B2
(45) Date of Patent: Jun. 23, 2015

(54) CAPACITIVE FILTERED FEEDTHROUGH ARRAY FOR IMPLANTABLE MEDICAL DEVICE

(75) Inventors: Rajesh V. Iyer, Eden Prairie, MN (US); Thomas P. Miltich, Otsego, MN (US); Gordon O. Munns, Stacy, MN (US); Simon E. Goldman, St. Louis Park, MN (US)

(73) Assignee: Medtronic, Inc., Minneapolis, MN (US)

( * ) Notice: Subject to any disclaimer, the term of this patent is extended or adjusted under 35 U.S.C. 154(b) by 373 days.

(21) Appl. No.: 13/596,944

(22) Filed: Aug. 28, 2012

(65) Prior Publication Data
US 2013/0127567 A1 May 23, 2013

Related U.S. Application Data

(60) Provisional application No. 61/530,249, filed on Sep. 1, 2011.

(51) Int. Cl.
*H03H 7/01* (2006.01)
*A61N 1/375* (2006.01)
(Continued)

(52) U.S. Cl.
CPC ........... *A61N 1/3754* (2013.01); *H03H 7/0138* (2013.01); *H05K 13/00* (2013.01); *Y10T 29/49165* (2015.01); *Y10T 29/435* (2015.01); *Y10T 29/43* (2015.01); *Y10T 29/49002* (2015.01); *Y10T 29/49171* (2015.01); *Y10T 29/49208* (2015.01); *H03H 2001/0042* (2013.01); *A61N 1/3968* (2013.01)

(58) Field of Classification Search
CPC .................... H03H 7/0138; H03H 2001/0042; A61N 1/3754
USPC .......................................................... 333/182
See application file for complete search history.

(56) References Cited

U.S. PATENT DOCUMENTS 3,617,830 A 11/1971 Perna
3,920,888 A 11/1975 Barr
(Continued)

FOREIGN PATENT DOCUMENTS

EP 1977786 A3 11/2011
JP 06120074 A 4/1994
(Continued)

OTHER PUBLICATIONS

Response to Office Action dated Apr. 16, 2013, from U.S. Appl. No. 13/346,424, filed Jul. 15, 2013, 11 pp.
(Continued)

*Primary Examiner* — Benny Lee
*Assistant Examiner* — Rakesh Patel

(57) ABSTRACT

In one example, a filtered feedthrough assembly for a medical device, such as, e.g., an implantable medical device, is described. The filtered feedthrough assembly may comprise a feedthrough comprising at least one feedthrough conductive pathway extending between a first feedthrough side and a second feedthrough side; a capacitive filter array comprising at least one filter array conductive pathway extending between a first filter array side and a second filter array side, and at least one capacitor filter substantially surrounding at least a portion the at least one filter array conductive pathway; and at least one electrically conductive member electrically coupling the at least one filter array conductive pathway to the at least one feedthrough conductive pathway.

39 Claims, 14 Drawing Sheets

(51) Int. Cl.
 *H05K 13/00* (2006.01)
 *A61N 1/39* (2006.01)
 *H03H 1/00* (2006.01)

(56) References Cited

U.S. PATENT DOCUMENTS

| | | | |
|---|---|---|---|
| 4,148,003 A | 4/1979 | Colburn et al. |
| 4,152,540 A | 5/1979 | Duncan et al. |
| 4,420,652 A | 12/1983 | Ikeno |
| 4,421,947 A | 12/1983 | Kyle |
| 4,424,551 A | 1/1984 | Stevenson et al. |
| 4,991,582 A | 2/1991 | Byers et al. |
| 5,287,076 A | 2/1994 | Johnescu et al. |
| 5,333,095 A | 7/1994 | Stevenson et al. |
| 5,434,358 A | 7/1995 | Glahn et al. |
| 5,440,447 A | 8/1995 | Shipman et al. |
| 5,470,345 A | 11/1995 | Hassler et al. |
| 5,620,476 A | 4/1997 | Truex et al. |
| 5,650,759 A | 7/1997 | Hittman et al. |
| 5,683,435 A | 11/1997 | Truex et al. |
| 5,685,632 A | 11/1997 | Schaller et al. |
| 5,735,884 A | 4/1998 | Thompson et al. |
| 5,750,926 A | 5/1998 | Schulman et al. |
| 5,751,539 A | 5/1998 | Stevenson et al. |
| 5,759,197 A | 6/1998 | Sawchuk et al. |
| 5,782,891 A | 7/1998 | Hassler et al. |
| 5,825,608 A | 10/1998 | Duva et al. |
| 5,836,992 A | 11/1998 | Thompson et al. |
| 5,866,851 A | 2/1999 | Taylor et al. |
| 5,867,361 A | 2/1999 | Wolf et al. |
| 5,870,272 A | 2/1999 | Seifried et al. |
| 5,896,267 A | 4/1999 | Hittman et al. |
| 5,905,627 A | 5/1999 | Brendel et al. |
| 5,959,829 A | 9/1999 | Stevenson et al. |
| 5,973,906 A | 10/1999 | Stevenson et al. |
| 5,999,398 A | 12/1999 | Makl et al. |
| 6,008,980 A | 12/1999 | Stevenson et al. |
| 6,031,710 A | 2/2000 | Wolf et al. |
| 6,275,369 B1 | 8/2001 | Stevenson et al. |
| 6,351,368 B1 | 2/2002 | Kim |
| 6,414,835 B1 | 7/2002 | Wolf et al. |
| 6,529,103 B1 | 3/2003 | Brendel et al. |
| 6,566,978 B2 | 5/2003 | Stevenson et al. |
| 6,643,903 B2 | 11/2003 | Stevenson et al. |
| 6,660,116 B2 | 12/2003 | Wolf et al. |
| 6,888,715 B2 | 5/2005 | Stevenson et al. |
| 6,920,673 B2 | 7/2005 | Allen et al. |
| 7,035,076 B1 | 4/2006 | Stevenson |
| 7,068,491 B1 | 6/2006 | Burdon et al. |
| 7,196,899 B1 | 3/2007 | Feger et al. |
| 7,199,995 B2 | 4/2007 | Stevenson |
| 7,668,597 B2 | 2/2010 | Engmark et al. |
| 7,725,177 B2 | 5/2010 | Iyer |
| 7,928,818 B2 | 4/2011 | Iyer |
| 8,536,468 B2 | 9/2013 | Teske |
| 2002/0027484 A1 | 3/2002 | Stevenson et al. |
| 2007/0060970 A1 | 3/2007 | Burdon et al. |
| 2007/0203529 A1 | 8/2007 | Iyer et al. |
| 2008/0195180 A1 | 8/2008 | Stevenson et al. |
| 2009/0079517 A1 | 3/2009 | Iyer |
| 2009/0079518 A1 | 3/2009 | Iyer |
| 2009/0187229 A1 | 7/2009 | Lavie |
| 2009/0281603 A1 | 11/2009 | Lim |
| 2010/0202096 A1 | 8/2010 | Iyer |
| 2010/0284124 A1 | 11/2010 | Iyer |
| 2011/0029036 A1 | 2/2011 | Yamamoto et al. |
| 2011/0048770 A1 | 3/2011 | Reiterer et al. |
| 2011/0102967 A1 | 5/2011 | Munns et al. |
| 2013/0009727 A1* | 1/2013 | Bultitude et al. ............. 333/185 |
| 2013/0058003 A1 | 3/2013 | Iyer et al. |
| 2014/0269220 A1* | 9/2014 | Tamura ........................ 368/47 |

FOREIGN PATENT DOCUMENTS

| | | |
|---|---|---|
| JP | 06244057 A | 9/1994 |
| WO | 9738752 A2 | 10/1997 |
| WO | 2009/117599 A2 | 9/2009 |
| WO | 2010129731 A2 | 11/2010 |
| WO | WO 2011/014399 A1 | 2/2011 |
| WO | WO 2011/025667 A1 | 3/2011 |

OTHER PUBLICATIONS

U.S. Appl. No. 13/196,661, by Kengo Morioka, filed Aug. 2, 2011.
U.S. Appl. No. 13/196,683, by Kengo Morioka, filed Aug. 2, 2011.
U.S. Appl. No. 13/196,695, by Kengo Morioka, filed Aug. 2, 2011.
U.S. Appl. No. 13/149,600, by Rajesh V. Iyer, filed May 31, 2011.
U.S. Appl. No. 13/308,136, by Rajesh V. Iyer, filed Nov. 30, 2011.
U.S. Appl. No. 13/308,222, by Rajesh V. Iyer, filed Nov. 30, 2011.
U.S. Appl. No. 13/346,424, by Rajesh V. Iyer, filed Jan. 9, 2012.
U.S. Appl. No. 13/308,271, by Rajesh V. Iyer, filed Nov. 30, 2011.
U.S. Appl. No. 13/308,144, by Rajesh V. Iyer, filed Nov. 30, 2011.
U.S. Appl. No. 13/308,313, by Rajesh V. Iyer, filed Nov. 30, 2011.
Office Action from U.S. Appl. No. 13/346,424, dated Sep. 9, 2013, 10 pp.
Office Action from U.S. Appl. No. 13/346,424, dated Apr. 16, 2013, 11 pp.
Response to Ex Parte Quayle Action dated Apr. 18, 2014, from U.S. Appl. No. 13/308,136, filed Apr. 30, 2014, 6 pp.
(PCT/US2012/052607) PCT Notification of Transmittal of the International Search Report and the Written Opinion of the International Searching Authority, Mailed Apr. 18, 2013, 13 pages.
Office Action from U.S. Appl. No. 13/308,222, dated Jan. 31, 2014, 49 pp.
Office Action from U.S. Appl. No. 13/308,136, dated Jan. 31, 2014, 6 pp.
Response to Office Action dated Sep. 9, 2013, from U.S. Appl. No. 13/346,424, filed Oct. 1, 2013, 5 pp.

* cited by examiner

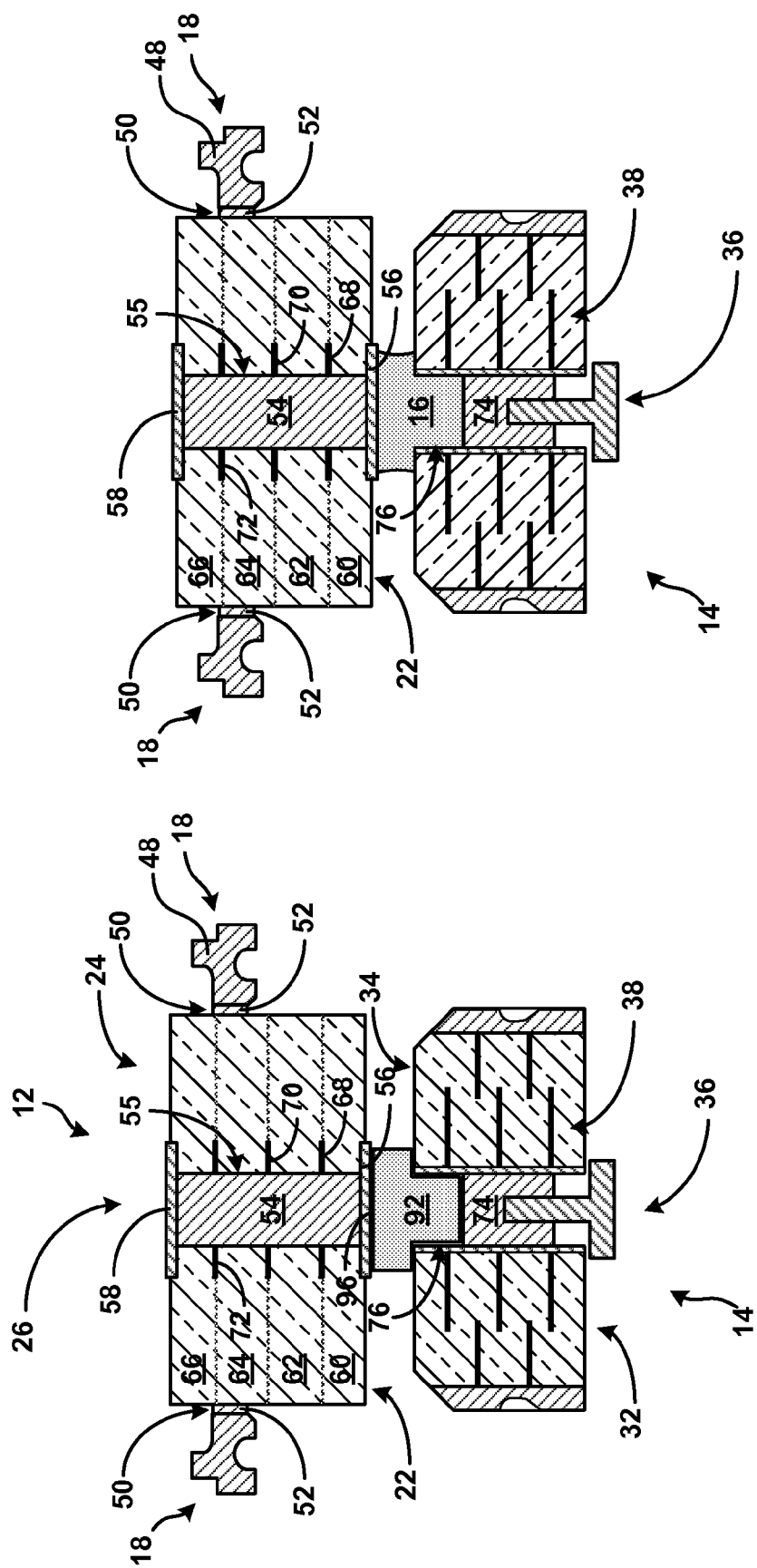

CAPACITIVE FILTERED FEEDTHROUGH ARRAY FOR IMPLANTABLE MEDICAL DEVICE

This application claims the benefit of U.S. Provisional Application No. 61/530,249, entitled, "CAPACITIVE FILTERED FEEDTHROUGH ARRAY FOR IMPLANTABLE MEDICAL DEVICE," and filed on Sep. 1, 2011, the entire content of which is incorporated herein by reference.

TECHNICAL FIELD

The present disclosure relates to electrical feedthroughs for electrically coupling an interior and an exterior of an electronics device, particularly electrical feedthroughs for use with implantable medical devices.

BACKGROUND

Electrical feedthroughs may provide an electrical pathway between an interior of a hermetically-sealed housing of an electronics device to a point outside the housing. For example, implantable medical devices (IMDs), such as implantable stimulation devices, implantable sensing devices, cardiac pacemakers, implantable cardioverter/defibrillators (ICDs) and neuromodulators, may use one or more electrical feedthroughs to make electrical connections between electrical circuitry within the implantable medical device and leads, electrodes, or sensors external to the device within a patient.

SUMMARY

In general, the present disclosure is directed to a capacitive filtered feedthrough assembly to provide at least one hermetically sealed conductive pathway filtered by a capacitive filter. The at least one hermetically sealed feedthrough conductive pathway may be formed in a cofired ceramic substrate comprising the at least one feedthrough conductive pathway. The capacitive filter array may comprise at least one filter array conductive pathway electrically coupled to the at least one feedthrough conductive pathways and at least one filter capacitor surrounding at least a portion of the at least one filter array conductive pathway or ground. In one example, the at least one filter array conductive pathway comprises a via extending through the capacitive filter array with a termination plug comprising an electrically conductive material substantially filling at least a portion of the via. The filtered feedthrough assembly may also include at least one electrically conductive member between the at least one feedthrough conductive pathway and the at least one filter array conductive pathway to electrically couple the respective pathways to each other.

In one example, the disclosure relates to a filtered feedthrough assembly comprising a feedthrough comprising at least one feedthrough conductive pathway extending between a first feedthrough side and a second feedthrough side; a capacitive filter array comprising at least one filter array conductive pathway extending between a first filter array side and a second filter array side, and at least one capacitor filter substantially surrounding at least a portion the at least one filter array conductive pathway; and at least one electrically conductive member electrically coupling the at least one filter array conductive pathway to the at least one feedthrough conductive pathway.

In another example, the disclosure relates to an implantable medical device comprising a housing; electronics enclosed within the housing; a ferrule mounted within an opening in the housing, the ferrule comprising a ferrule opening extending between an internally-facing ferrule side and an externally-facing ferrule side; a feedthrough mounted in the ferrule opening, wherein a hermetic seal is formed between the feedthrough and the ferrule, the feedthrough comprising at least one feedthrough conductive pathway extending through the feedthrough between an internally-facing feedthrough side and an externally-facing feedthrough side; a capacitive filter array comprising at least one filter array conductive pathway extending between an internally-facing filter array side and an externally-facing filter array side, and at least one capacitor filters substantially surrounding at least a portion of the at least one filter array conductive pathway; at least and one electrically conductive member electrically coupling the at least one filter array conductive pathway to the at least one feedthrough conductive pathways.

In another example, the disclosure relates to a method comprising electrically coupling at least one feedthrough conductive pathway of a feedthrough to at least one filter array conductive pathway of a capacitive filter array via at least one electrically conductive member, wherein the at least one feedthrough conductive pathway extends between a first feedthrough side and a second feedthrough side, and wherein the at least one filter array conductive pathway extends between a first filter array side and a second filter array side, and the capacitive filter array comprises at least one capacitor filter substantially surrounding at least a portion the at least one filter array conductive pathway.

The details of one or more examples of the disclosure are set forth in the accompanying drawings and the description below. Other features, objects, and advantages of the disclosure will be apparent from the description and drawings, and from the claims.

BRIEF DESCRIPTION OF DRAWINGS

FIGS. 7A-7C are cross-sectional views illustrating the example feedthrough assembly of FIG. 1 at various stages of a example technique of attaching an example feedthrough to an example filter array.

DETAILED DESCRIPTION

Figure 1:
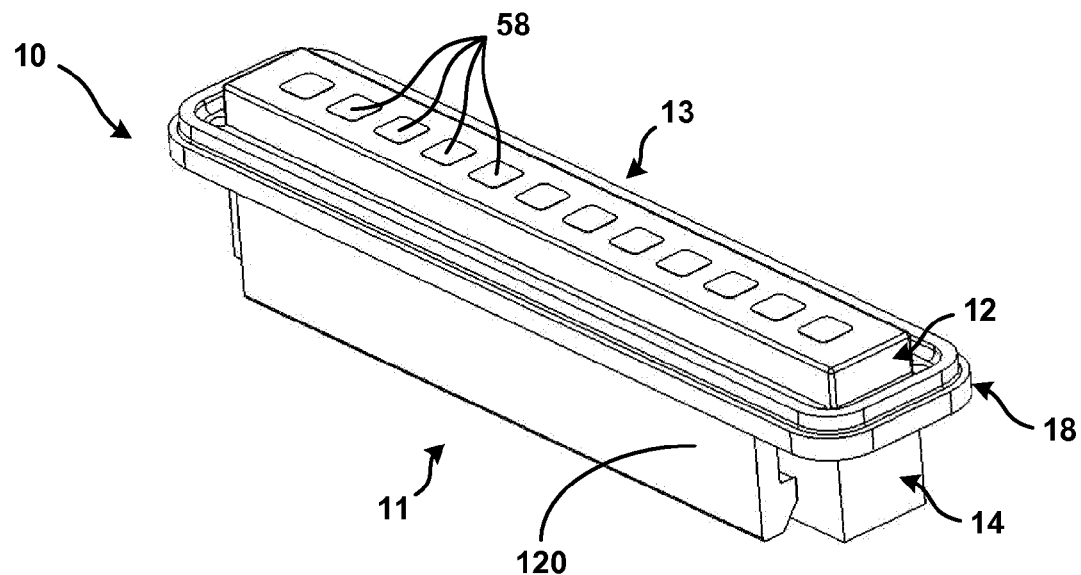
FIG. 1 is a perspective view illustrating an externally-facing side of an example feedthrough assembly that may be used with an implantable medical device.

In general, the present disclosure is directed to techniques for attaching a feedthrough that provides for the passage of electrical signals from inside an electronics device housing to outside the electronics device housing, or vice versa, to a capacitive filter array. The capacitive filter array may provide filtering of electromagnetic interference (EMI) that may interfere with the normal operation of the electronics device. An electrically conductive member may electrically couple a feedthrough conductive pathway of the feedthrough to a corresponding conductive pathway of the capacitive filter array. In this manner, the electrically conductive member may be used to establish an electrical connection across a filtered feedthrough assembly via the individual conductive pathways of the feedthrough and capacitive filter array, e.g., rather than using a single conductive pin that extending through openings in the feedthrough and capacitive filter array.

Examples of electrical conductive members may include solder preforms used to form solder joints, coiled spring connectors, spring-loaded contact connectors (e.g., single or double pogo connectors), or other pressure contacts, conductive epoxies/polymers, scraping contacts, fuzz button interconnects, and the like. When positioned between the conductive pathways of the feedthrough and capacitive filter array such that a portion of the electrical conductive member is in contact with the conductive pathway of feedthrough and a portion of the electrically conductive member is in contact with a corresponding conductive pathway of the capacitive filter array, electrical current may be passed through the feedthrough and capacitive filter array via the formed conductive pathway. When such an assembly is incorporated into a medical device, for example, electrical current may be conducted from the externally-facing side of a feedthrough to the internally-facing side of the capacitive filter array via the conductive pathway, and vice versa.

In some examples, in addition to electrically coupling feedthrough conductive pathways to corresponding capacitive filter array conductive pathway in a filtered feedthrough assembly, the electrically conductive member may act to mechanically couple the feedthrough assembly to the capacitive filter array. For example, an internally-facing side of the feedthrough may be attached to an externally-facing side of the filter array with at least one solder joint that mechanically couples and electrically couples a corresponding feedthrough conductive pathway to a corresponding filter array conductive pathways. The solder joint may be formed by positioning a solder preform between the feedthrough conductive pathway and the filter array conductive pathway and melting the solder preform to form the solder joint. Additionally or alternatively, a feedthrough and capacitive filter array may be mechanically coupled via other techniques, such as, e.g., one or more braze joints. In some examples, the electrically conductive member may not provide for any substantial mechanical coupling but primarily serve to electrically couple conductive pathways of the feedthrough and capacitive filter array to each other.

In some examples, such an electrically conductive member may be configured to align conductive pathways of a feedthrough with corresponding conductive pathways of a capacitive filter array when the feedthrough assembly is being assembly. For example, in one example, a solder preform may comprise an alignment portion that is registered with a portion of either the capacitive filter array or the feedthrough, or both, so that each preform is substantially aligned with its corresponding feedthrough conductive pathway and/or filter array conductive pathway prior to melting the solder preform to form a solder joint. In some cases, the feedthrough and/or capacitive filter array may include recesses into opposing surfaces adjacent to conductive pathways such that the electrically conductive member may mate within the recess and protrude from the surface to assist with the alignment of conductive pathways of the feedthrough and capacitive filter array during assembly.

In some cases, electrical feedthroughs may provide an electrical pathway between an interior of a hermetically-sealed housing of an electronics device to a point outside the housing. For example, implantable medical devices (IMDs), such as implantable stimulation devices, implantable sensing devices, cardiac pacemakers, and implantable cardioverter/defibrillators (ICDs) use one or more electrical feedthroughs to make electrical connections between electrical circuitry within the implantable medical device and leads, electrodes, or sensors external to the device within a patient. A feedthrough may comprise a ferrule that is mounted within an opening in the housing, such as by welding the ferrule into the housing opening, a conductor surrounded by an insulator passing through the ferrule, and a hermetic seal using glass, braze, elastomer, or ceramic seal, that mechanically joins the insulator to the ferrule.

Previously, implantable medical devices comprised relatively large housings and employed a small number of leads such that each conductor exiting the IMD was facilitated by a single-conductor feedthrough. As IMDs have been developed, the electronics within the IMD have been reduced in size, permitting the use of dramatically smaller housing sizes. Also, the number of external leads, electrodes, or sensors that are coupled to a common IMD has increased. Therefore, in some examples, the use of single-conductor feedthroughs may no longer be practical for many IMDs. In some examples, multi-conductor feedthroughs can provide hermetic pathways for a plurality of conductors (e.g., four or more) through smaller openings within the IMD housing. An example multi-conductor feedthrough may comprise a ceramic substrate mounted within a ferrule, wherein the ceramic substrate comprises a plurality of conductive pathways, such as traces or vias, formed in the ceramic substrate.

In many cases, an IMD is implanted at a different location within the patient as the target tissue that is being stimulated and/or diagnosed. Elongated leads may carry electrical conductors that extend from the electrodes or sensors located at the target tissue to the IMD, wherein the electrical conductors pass through a feedthrough or are electrically coupled to a conductive path through the feedthrough. The elongated lead conductors may effectively act as antennae that collect stray electromagnetic interference (EMI) signals that may be transmitted along the lead conductor into the IMD. In some cases, the EMI may interfere with normal IMD operations. For example, at certain frequencies, EMI may be interpreted as telemetry signals that may cause the IMD to inadvertently change operating mode or undesirably diagnose an adverse event causing an undesired change in therapy.

In some case, such issues with EMI has been addressed by incorporating a capacitor structure, such as a discoidal capacitive filter, at an internally facing portion of the feedthrough that filters out high-frequency EMI transmitting from the external lead conductor through the feedthrough conductor. In some cases, capacitive filter arrays have been developed to accommodate multiple lead conductors and a corresponding multi-conductor feedthrough. The capacitive filter array may be attached to the multi-conductor feedthrough so that each of the conductive pathways through the multi-conductor feedthrough may be electrically coupled to a corresponding conductive path in the capacitive filter array while still providing for a hermetic seal around each conductive pathway and between the multi-conductor feedthrough and the ferrule.

As described below, some examples of the present disclosure relate to feedthrough assemblies including a feedthrough comprising a plurality of feedthrough conductive pathways each electrically coupled to corresponding filter array conductive pathways of capacitive filter array via a corresponding electrically conductive member. In this manner, the plurality of electrically conductive members may provide a relatively easy-to-form, and relatively inexpensive method of coupling a feedthrough to a capacitive filter array without the need for expensive ceramic or metal processing techniques. For example, conductive pins extending entirely through the filtered feedthrough assembly may not be needed as conductive pathways through the assembly by electrically coupling conductive pathways of a feedthrough to corresponding conductive pathways of a capacitive filter array via an electrically conductive member positioned between the respective pathways.

In the disclosure, for ease of illustration, examples are initially primarily described with regard to electrically conductive members comprising solder performs and solder joints. However, examples are not limited as such. As will be described below, any suitable electrically conductive member may be used, and may include coiled spring connectors, spring-loaded contact connectors (e.g., single or double pogo connectors), or other pressure contacts, conductive epoxies/polymers, scraping contacts, fuzz button interconnects, and the like.

Figure 2:
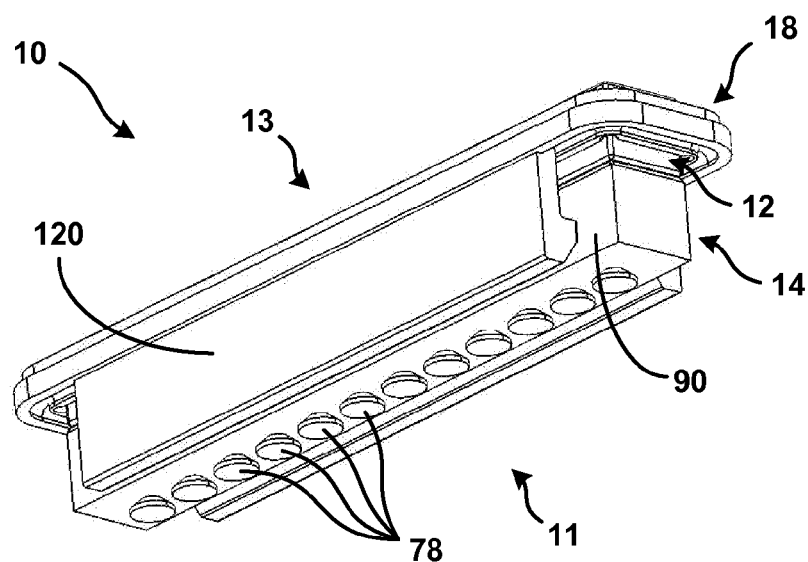
FIG. 2 is a perspective view illustrating an internally-facing side of the example feedthrough assembly of FIG. 1.
Figure 3:
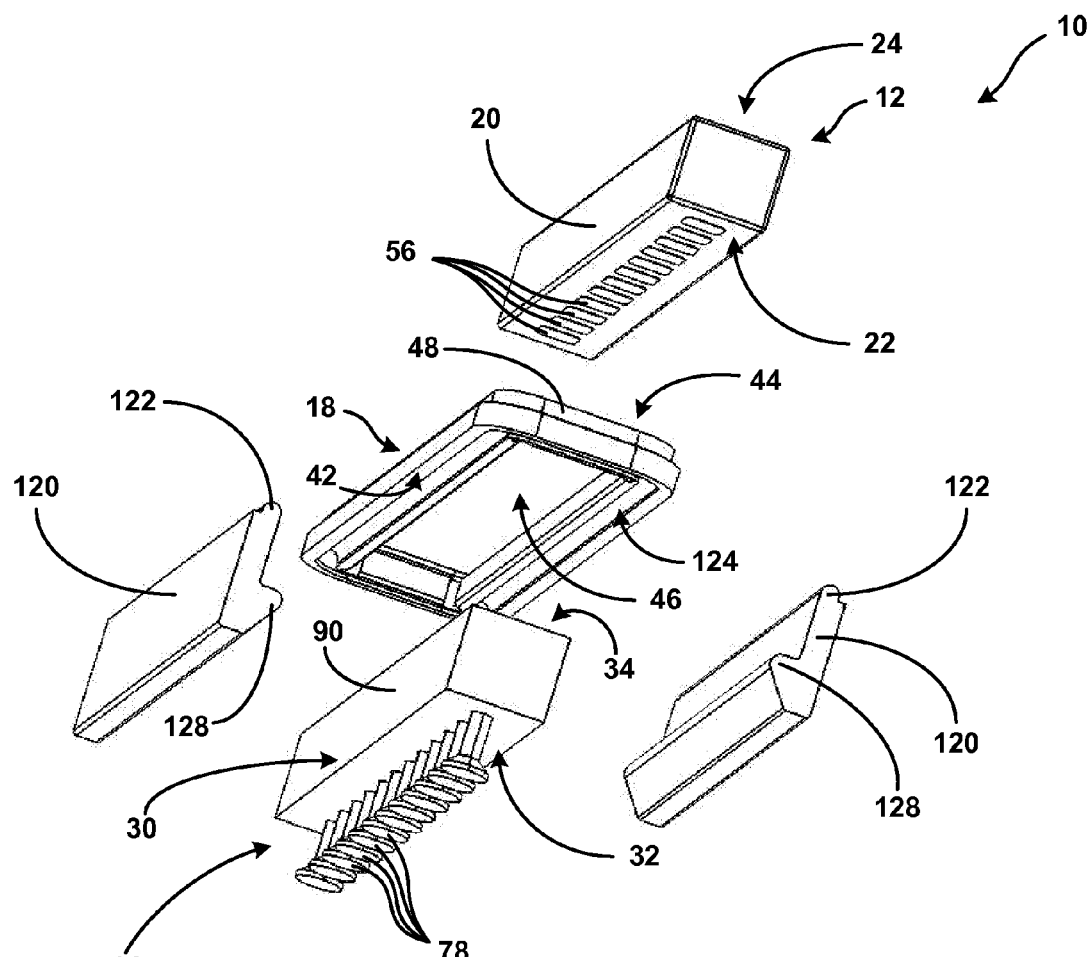
FIG. 3 is an exploded perspective view illustrating the example feedthrough assembly of FIG. 1.
Figure 4:
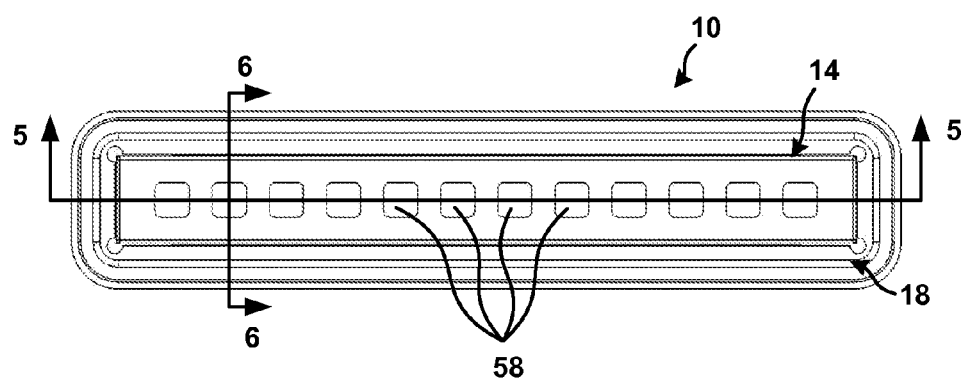
FIG. 4 is a plan view illustrating the example feedthrough assembly of FIG. 1.
Figure 5:
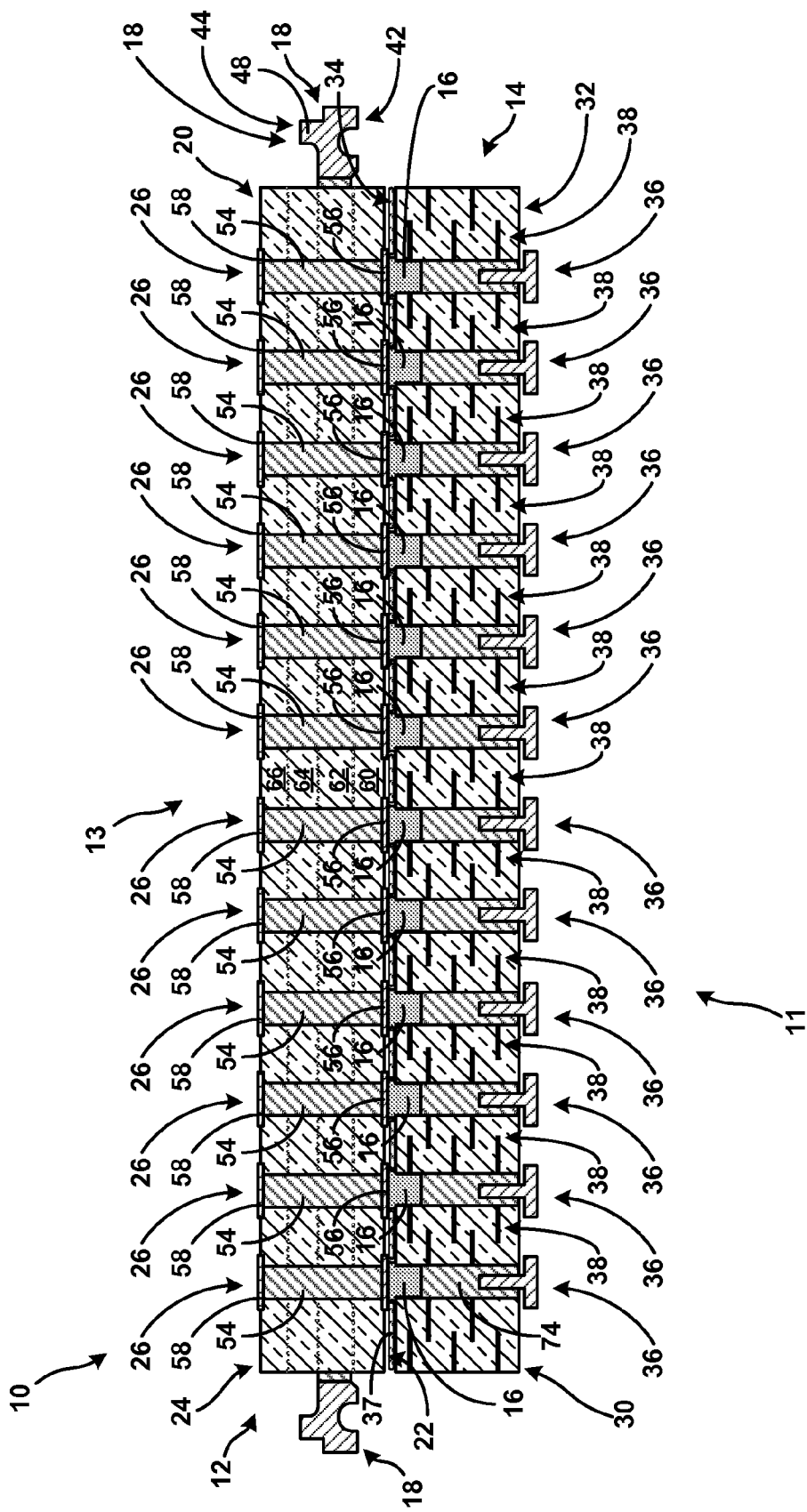
FIG. 5 is a cross-sectional view of the example feedthrough assembly of FIG. 1 taken along line 5-5 of FIG. 4.
Figure 6:
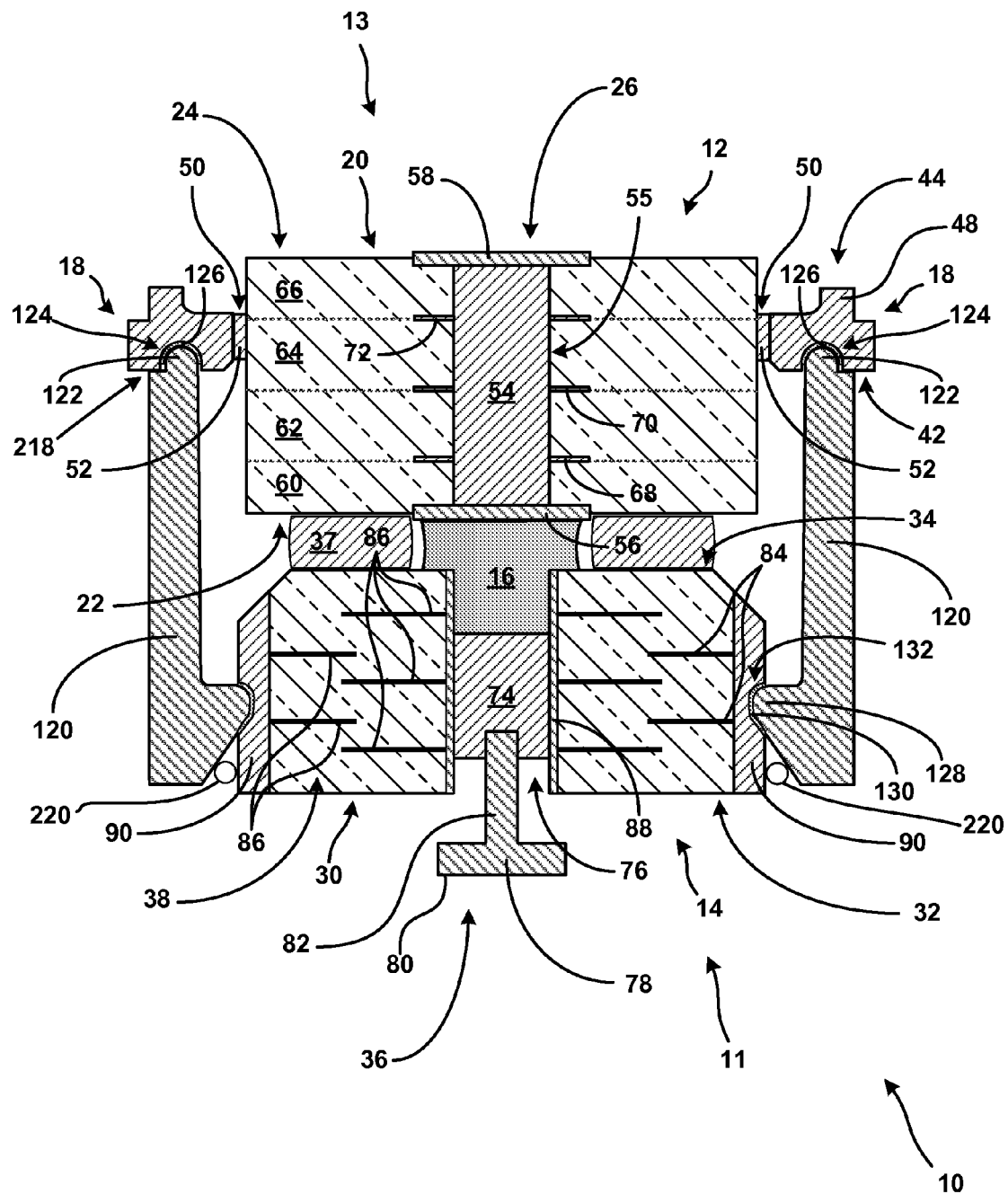
FIG. 6 is a cross-sectional view of the example feedthrough assembly of FIG. 1 taken along line 6-6 of FIG. 4.

FIG. 1 is a perspective view of an example, filtered feedthrough assembly 10. Feedthrough assembly 10 includes an internally-facing side 11 and an externally-facing side 13. FIG. 2 shows another perspective view of feedthrough assembly 10 showing the internally-facing side 11 of feedthrough assembly 10. FIG. 3 shows an exploded perspective view of feedthrough assembly 10. FIG. 4 is a plan view of externally-facing side 13 of feedthrough assembly 10. The terms "internally-facing," "inwardly," and the like, when used herein in regards to feedthrough assembly 10 may generally refer to a direction toward the interior of an electronics device (e.g., an IMD) when assembly 10 is incorporated in the electronics device. Conversely, the terms "externally-facing," "outwardly," and the like, when used herein in regards to feedthrough assembly 10 generally refer to a direction toward the exterior of the electronics device when assembly 10 is incorporated in the electronics device. As shown, feedthrough assembly 10 comprises a feedthrough 12 and a capacitive filter array 14. Feedthrough 12 may be coupled to capacitive filter array 14 by a plurality of electrically conductive members in the form of plurality of solder joints 16 (e.g., as shown in FIGS. 5 and 6) that are formed between feedthrough 12 and capacitive filter array 14. Feedthrough 12 is mounted within a ferrule 18 that is mountable within an opening formed in the housing of an electronics device, such as an IMD.

Ferrule 18 comprises an internally-facing ferrule side 42 and an externally facing ferrule side 44, and a ferrule opening 46 (FIG. 3) that extends between internally-facing side 42 and externally-facing side 44. Ferrule 18 may also comprise a mounting flange 48 for mounting ferrule 18 within the housing of the electronics device, such as an IMD. Flange 48 may be mounted to the IMD housing, for example, by welding or brazing.

In one example, ferrule 18 comprises a material that can easily be mounted to the housing of an IMD. For example, in some examples the IMD housing may comprise titanium or a titanium alloy, and ferrule 18 may comprise titanium or a titanium alloy that can be welded to the material of IMD housing. Examples of materials that may be used to make ferrule 18 include, but are not limited to, niobium, titanium, titanium alloys such as titanium-6Al-4V or titanium-vanadium, platinum, molybdenum, zirconium, tantalum, vanadium, tungsten, iridium, rhodium, rhenium, osmium, ruthenium, palladium, silver, and alloys, mixtures, and combinations thereof. In one example, the material of ferrule 18 is selected so that ferrule 18 has a coefficient of thermal expansion (CTE) that is compatible with the CTE of feedthrough 12. In this manner, damage resulting from the heating of ferrule 18 and feedthrough 12, such as during the formation of a diffusion bonded, glassed, or brazed joint between ferrule 18 and feedthrough 12, may be prevented or minimized.

Feedthrough 12 may be mounted within ferrule opening 46 with a hermetic seal 50 formed between feedthrough 12 and ferrule 18 (see, e.g., FIG. 6). Hermetic seal 50 may prevent the passage of bodily fluids of the patient from passing into the interior of IMD housing between ferrule 18 and feedthrough 12, which could lead to damage to the internal electronics of IMD. In one example, hermetic seal 50 comprises a braze joint between feedthrough 12 and ferrule 18. In other examples, the joint may be formed using a biocompatible, biostable or by diffusion bonding. Examples of materials that may be used to form a hermetically-sealed braze joint 52 include, but are not limited to, gold, a nickel-gold alloy, platinum, and platinum-iridium. Diffusion bonding, laser brazing, or laser sintering of glass may also be used to bond feedthrough 12 to ferrule 18.

FIG. 5 is a cross-sectional side view of feedthrough assembly 10 and FIG. 6 is a cross-sectional end view of feedthrough assembly 10 along lines 5-5 and 6-6, respectively shown in FIG. 4. As shown in the example of FIGS. 5 and 6, feedthrough 12 may comprise a feedthrough substrate 20 comprising an internally-facing feedthrough substrate side 22 and a generally opposed externally-facing feedthrough substrate side 24. A plurality of feedthrough conductive pathways 26 extend through feedthrough substrate 20 between internally-facing side 22 and externally-facing side 24. Conductive pathways 26 may be substantially electrically isolated from one another by the material of feedthrough substrate 20.

Capacitive filter array 14 may comprise a capacitive filter substrate 30 comprising an internally-facing filter array side 32 and an externally-facing filter array side 34. A plurality of filter array conductive pathways 36 extend through capacitive filter substrate 30 between internally-facing side 32 and externally-facing side 34. Respective conductive pathways 36 in filter substrate 30 may be substantially electrically isolated from one another. Capacitive filter substrate 30 defines a plurality of capacitive filters, such as discoidal capacitor filters 38, arranged in an array 14, wherein each capacitor filter 38 substantially surrounds at least a portion of a corresponding conductive pathway 36 to filter EMI from signals that are passed through conductive pathways 26, 36.

In one example, an electrical insulation layer 37 (FIGS. 5 and 6) may be placed between feedthrough 12 and filter array 14 in order to reduce or prevent high-voltage arcing between feedthrough 12 and filter array 14. Insulation layer 37 may also be provided to prevent arcing between the conductive path (which may be continuous between the feedthrough pads and filter array) and ferrule 18, as any direct line of sight between the conductive pathway and ferrule 18 (or the filter cap outer diameter) may cause surface arcing. In this sense, insulation layer 37 may prevent surface arcing in such a gap.

In one example, insulation layer 37 comprises an electrically insulating material, such as an electrically insulating polymer formed on externally-facing side 34 of filter array 14 (e.g., using an underfill process). Because portions of insulation layer 37 may be located proximate solder joints 16 during the formation of solder joints 16, as described in more detail below, in one example, insulation layer 37 comprises a material that is able to withstand the melting temperature of the material of solder joints 16, e.g., wherein the melting temperature and glass transition temperature of the material of insulation layer 37 is higher than the melting temperature of the material of solder joint 16. As described in more detail below, the melting temperature of solder joints 16 may be between about 100° C. and about 350° C., so in such examples, the material of insulation layer 37 is capable of withstanding these temperatures. In one example, insulation layer 37 comprises a polyimide polymer with a glass transition temperature of greater than about 400° C. In some examples, insulating layer 37 may comprise a low temperature cofired ceramic material.

Feedthrough conductive pathways 26 provide for an electrical pathway for electrical signals to be transmitted across feedthrough substrate 20, such as stimulation signals transmitted from electronics within an IMD housing for stimulation of a target tissue, or bioelectric signals sensed proximate a target tissue that are transmitted into the IMD housing for analysis by IMD electronics. In one example, each conductive pathway 26 comprises a via 54 that passes through feedthrough substrate 20 between internally-facing side 22 and externally facing side 24. Via 54 may comprise a conductive material, such as a metal or alloy, that substantially fills a hole extending through feedthrough substrate 20. In one example, a hermetic seal 55 is formed at the interface between each via 54 and feedthrough substrate 20 (FIG. 6). Hermetic seal 55 may be formed by many methods, such as by forming a braze joint between the material of via 54 and the material of feedthrough substrate 20. In one example, described in more detail below, hermetic seal 55 is formed by cofiring the materials of feedthrough substrate 20 and via 54 so that the material of via 54 bonds with the material of feedthrough substrate 20.

Each conductive pathway 26 may also comprise a contact pad 56 at internally-facing side 22, wherein each contact pad 56 provide a relative large area to provide for electrical and/or mechanical coupling between cofired substrate conductive pathway 26 and filter array conductive pathways 36. In one example, each internally-facing contact pad 56 is electrically and mechanically coupled to a corresponding via 54. Conductive pathway 26 may also comprise a contact pad 58 at externally-facing side 24, wherein each contact pad 58 provides a relatively large surface are to provide for electrical and/or mechanical coupling of a conductor, such as a lead conductor for an IMD, to conductive pathway 26. In one example, each contact pad 58 is electrically and mechanically coupled to a corresponding via 54.

In some examples, vias 54 and contact pads 56, 58 each comprise an electrically conducting material, such as a conductive metal or alloy. Examples of conductive materials that may be used for vias 54 and contact pads 56, 58 include, but are not limited to, transition metals (e.g., noble metals), rare-earth (e.g., actinide metals and lanthanide metals), alkali metals, alkaline-earth metals, and rare metals. Examples of materials that may be used include, but are not limited to, copper (Cu), silver (Ag), gold (Au), platinum (Pt), palladium (Pd), niobium (Nb), iridium (Ir), titanium (Ti), tungsten (W), molybdenum (Mb), zirconium (Zr), osmium (Os), tantalum (Ta), vanadium (V), rhodium (Rh), rhenium (Re), and ruthenium (Ru), platinum-gold alloys, platinum-iridium alloys, platinum-palladium alloys, gold-palladium alloys, titanium alloys, such as Ti-6Al-4V, Ti-45Nb, Ti-15Mo or titanium-vanadium, tungsten-molybdenum alloys, and alloys, mixtures, and combinations thereof.

With respect to internally-facing contact pad 56, in some examples, the material and structure of contact pad 56 may be selected to support bonding of a corresponding solder joint 16 to provide electrical and mechanical coupling between contact pad 56 and solder joint 16. With respect to externally-facing contact pad 58, the material and structure of contact pad 56 are selected to support welding of a conductor, such as a wire or conductor used in a lead for an IMD, to an external surface of contact pad 58. Examples of materials that may be used in an IMD lead conductor that may be welded to contact pad 58 include, but are not limited to, niobium (Nb), a MP35N or MP35NLT nickel-based alloy, silver core Co—Cr—Ni alloy, tantalum, silver core Ta, Ti, Ti-45Nb, Ti—Mo alloys, and alloys meeting ASTM standard F562. Examples of welding processes that may be used to weld the lead conductor to contact pad 58 include, but are not limited to, laser welding, parallel gap welding, thermosonic bonding, diffusion bonding, ultrasonic welding, opposed gap welding, laser brazing, step gap resistance welding, brazed interposer, percussion arc welding, or soldering (conventional or laser).

In one example, feedthrough substrate 20 comprises multi-layer ceramic formed from a plurality of generally planar ceramic layers 60, 62, 64, 66. Although only four ceramic layers 60, 62, 64, 66 are shown in FIGS. 5 and 6, more or fewer ceramic layers may be used to form feedthrough substrate 20. Each ceramic layer 60, 62, 64, 66 is shaped in a green state to have a layer thickness and a plurality of via holes extending there through between an internally facing layer surface and an externally facing layer surface. Ceramic layers 60, 62, 64, 66 are coupled together, such as by laminating layers 60, 62, 64, 66 together, and may be cofired together so that layers 60, 62, 64, 66 form a substantially monolithic substrate body 20. In one example, the via holes of each layer 60, 62, 64, 66 are substantially aligned to form generally cylindrical vias 54 that are filled with metal to form conductive pathways 26.

In one example, feedthrough substrate 20 may comprise a high-temperature cofired ceramic (HTCC) material, e.g., a ceramic that is sintered at a temperature of at least about 1300° C., for example a material that is sintered at a temperature of at least about 1600° C. In some embodiments, HTCC uses 1) an electrical insulator that includes alumina and may include oxides of Si (silica), Ca (calcium), Mg (magnesia), Zr (zirconia), and the like and 2) an electrical conductor, such as platinum or Pt—Ir. The assembly of which can be fired (sintered) above 1000 C, such as about 1600 C. In this sintering process polymeric binders may be driven off and the particles forming the ceramic and metal coalesce and fuse. Grains diffuse together forming larger grains at the expense of smaller grains.

In one example, feedthrough substrate 20 comprises an HTCC liquid-phase, sintered alumina with platinum metallization. In one example, feedthrough substrate 20 may comprise at least about 70% alumina, for example at least about 90% alumina having a sintering temperature of between about 1550° C. and about 1600° C. In some examples, feedthrough substrate 20 consists essentially of a high-temperature cofired ceramic, and in some examples, feedthrough substrate 20 consists of a high-temperature cofired ceramic.

In some examples in which feedthrough substrate 20 comprises a HTCC material, conductive pathways 26 may comprise a conductive paste that is used to fill via holes to form vias 54. The conductive paste may comprise, for example, a metallic paste that is applied to the via holes, for example a platinum-containing paste, a tungsten-containing paste, Nb-containing paste, Ta-containing paste, Au-containing paste, or a molymanganese-containing paste. Such may materials may be biocompatible and biostable materials. In one example, the metallic paste primarily comprises a metallic powder, such as platinum powder, and an additive to promote bonding with the material of feedthrough substrate 20. The additive may also provide for thermal expansion compatibility between the conductive paste of vias 54 and the HTCC material of feedthrough substrate 20. In one example, the additive comprises alumina, so that the metallic paste may comprise, for example, a majority of metallic powder, such as platinum powder, and a minority of alumina powder or particles mixed therein.

In one example, a via 54 formed from a conductive paste, such as a platinum and alumina containing paste, and a feedthrough substrate 20 comprising an HTCC material, such as a sintered alumina, are cofired together, e.g., at a temperature of around 1600° C., so that the conductive paste and HTCC material bond together to form hermetic seal 55. In some examples, the additive of the conductive paste is compatible with the HTCC material of feedthrough substrate 20, such as when both the HTCC material and the additive comprise alumina, to form an interfaced (e.g., bonded) hermetic seal 55 between via 54, formed from the conductive paste, and feedthrough substrate 20, formed from the HTCC material. In such an example, hermetic seal 55 is formed between via 54 and feedthrough substrate 20 without the need of a separate joining material, such as a braze joint between the electrically conductive via 54 and the electrically insulating feedthrough substrate 20.

In one example, as shown in FIG. 6, a feedthrough substrate 20 formed from a plurality of layers 60, 62, 64, 66 of an HTCC material may further comprise a plurality of cover pads 68, 70, 72, wherein each internal cover pad 68, 70, 72 is coupled to a corresponding layer 62, 64, 66 of feedthrough substrate 20. In one example, each internal cover pad 68, 70, 72 overlays a corresponding layer 62, 64, 66 (respectively) and substantially radially surrounds a via within layers 62, 64, 66, wherein the via holes are filled with a conductive material, as described above, to form via 54. Examples of materials that may be used to form internal cover pads 68, 70, 72 include, but are not limited to, platinum metal, tungsten metal, niobium, and the like. In some examples, cover pads 68, 70, 72 may be formed of multiple prints of platinum past. Cover pads 68, 70, 72 may be radially symmetric or asymmetric, and may radially surround the via within layers 62, 64, 66.

Internal cover pads 68, 70, 72 may provide for improved electrically connectivity between the material of via 54, such as the conductive pastes described above, within adjacent layers 60, 62, 64, 66 of feedthrough substrate 20. For example, during formation of feedthrough substrate 20 by stacking layers 60, 62, 64, 66, the via holes of each layer 60, 62, 64, 66 may not be perfectly aligned. Internal cover pads 68, 70, 72 provide a structure that may provide for electrical coupling between the slightly non-aligned via holes to form a substantially continuous via 54.

Examples of materials and methods for making a cofired ceramic substrate are described in the commonly assigned U.S. Provisional Patent Application Ser. No. 61/238,515, filed on Aug. 31, 2009, the commonly assigned U.S. patent application Ser. No. 12/693,772, filed on Jan. 26, 2010, the commonly assigned U.S. Pat. No. 6,414,835, issued on Jul. 2, 2002, the commonly-assigned U.S. Pat. No. 6,660,116, issued on Dec. 9, 2003, U.S. Provisional patent application Ser. No. 13/196,661, filed on Aug. 2, 2011, U.S. Provisional patent application Ser. No. 13/196,683, filed on Aug. 2, 2011, and U.S. Provisional patent application Ser. No. 13/196,695, filed on Aug. 2, 2011, the disclosures of which are incorporated by reference as if reproduced herein.

As shown in FIG. 5, capacitive filter array 14 also comprises a plurality of conductive pathways 36 that provide an electrical pathway for electrical signals to be transmitted through filter array 14, such as stimulation signals transmitted from electronics within an IMD housing for stimulation of a target tissue or bioelectric signals sensed proximate a target tissue that are transmitted into the IMD housing for analysis by IMD electronics, so that the signals may be filtered by capacitive filters 38. In one example, each conductive pathway 36 comprises a via 74 formed within a via hole 76 (as shown, e.g., in FIGS. 6 and 7A) that passes from internally-facing side 32 to externally-facing side 34 of filter array 14.

In one example, as shown in FIG. 6, each via 74 comprises a plug 74 of a termination material, that is formed by forming the termination plug 74 within via hole 76. Examples of termination materials that may be used to form termination plug 74 include, but are not limited to, noble metals, such as gold (Au), silver (Ag), platinum (Pt), palladium (Pd), ruthenium (Ru), rhodium (Rh), osmium (Os), or iridium (Ir), or alloys thereof, such as silver-palladium alloy. In some examples, plug 74 may include a base substrate plated with one or more desired materials, such as those materials describe above. In one example, the material of termination plug 74 is fired at a temperature of at least about 500° C., such as at a temperature of about 800° C.

In one example, each filter array conductive pathway 36 may also comprise a lead frame 78 (as shown in FIG. 6) that provides a structure for electrically coupling conductive pathway 36 to internal electronics within the electronics device, such as to the circuitry within an IMD that provides an electrical stimulation signal to be transmitted through filter array 14 and feedthrough 12 to be delivered to a target tissue, or that receives and analyzes a sensed bioelectric signal transmitted from proximate the target tissue. In one example, lead frame 78 provides a relatively large, generally internally-facing surface 80 that provides for welding of a conductor that is electrically coupled to internal electronics of the IMD. In one example, shown in FIG. 6, a portion of lead frame 78, such as a stem 82, is embedded into via 74 so that lead frame 78 and via 74 are electrically and mechanically coupled to one another.

At least a portion of each via 74 is substantially radially surrounded by a corresponding capacitive filter 38 that provides for filtering of signals that are passing through the corresponding via 74. For example, each capacitive filter 38 may provide for filtering of current induced in an IMD lead by external electromagnetic fields so that the induced current is not inadvertently interpreted by the IMD circuitry as a signal, such as a telemetry signal. In one example, best shown in FIG. 6, each capacitive filter 38 comprises a plurality of layers (not shown) of ceramic, such as barium titanate, with conductive active electrodes 84 and ground electrodes 86 formed on the layers, such as by printing the material of electrodes 84, 86, for example silver, silver-palladium, or silver-platinum, onto the layers before stacking and laminating the layers. In one example, active electrodes 84 substantially radially surround a corresponding conductive pathway 36. Active electrodes 84 are electrically coupled to conductive pathway 36, such as by being electrically exposed to termination plug 74, or through a mechanical and electrical coupling structure such as a termination joint 88 that may be formed between termination plug 74 and the ceramic layers of capacitive filter 38. Ground electrodes 86 are electrically connected to a common ground, as described in more detail below, such as via a termination 90.

In accordance with one or more examples of the disclosure, feedthrough 12 may be electrically coupled to capacitive filter array 14 via an electrically conductive member, e.g., solder joints 16. Additionally or alternatively, as will be described below, feedthrough 12 may be electrically and/or mechanically coupled to filter array 14 via, e.g., coiled spring connectors, spring-loaded contact connectors (e.g., single or double pogo connectors), or other pressure contacts, conductive epoxies/polymers, scraping contacts, fuzz button interconnects, and lower temperature brazing. As further shown in FIG. 5, a plurality of solder joints 16 are formed between feedthrough 12 and capacitive filter array 14. Each solder joint 16 is formed between a corresponding cofired substrate conductive pathway 26 and a corresponding filter array conductive pathway 36 in order to mechanically couple and electrically couple the corresponding conductive pathways 26, 36 together. Solder joints 16 (as well as other example electrically conductive members described herein) may provide a relatively easy-to-form, and relatively inexpensive method of coupling feedthrough 12 to capacitive filter array 14.

In some examples, in addition to electrical coupling conductive pathways 26, 36 of feedthrough 12 and capacitive filter array 14, respectively, via an electrical conductive member, such an electrical conductive member may also at least partially mechanically couple feedthrough 12 and capacitive filter array 14 to each other. For example, solder joints 16 may comprise a material that is capable of providing mechanical coupling between feedthrough 12 and filter array 14. Solder joints 16 also comprise a material that is electrically conductive in order to electrically couple each feedthrough conductive pathway 26 with a corresponding filter array conductive pathway 36. Examples of materials that may be used to form solder joints 16 include, but are not limited to, indium-silver (In—Ag) alloys, tin-silver (Sn—Ag), tin-copper (Sn—Cu), tin-silver-copper (Sn—Ag—Cu), tin-lead (Sn—Pb), and gold-tin (Au—Sn). In one example, the material of solder joints 16 has a melting temperature of between about 150° C. and about 350° C. In one example, the melting temperature of the material of solder joints 16 is lower than a melting temperature of both via 74 and via 54 so that the formation of solder joints 16 does not interfere with the structural integrity of conductive pathways 26, 36 during the soldering process.

Figure 7A:
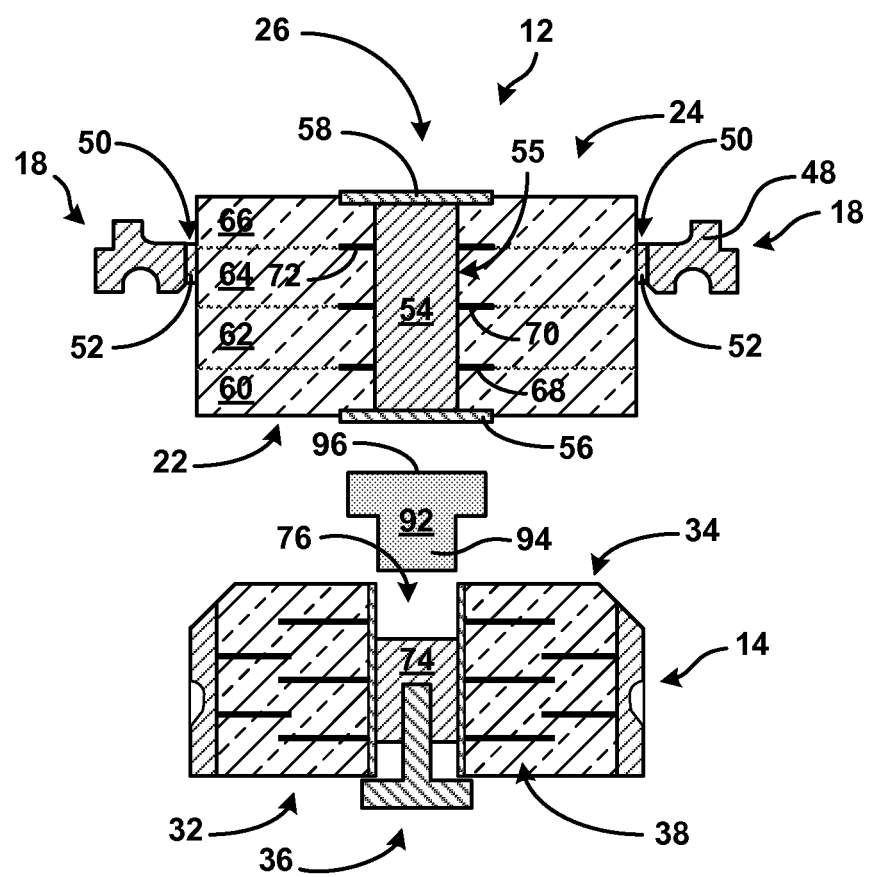

In one example, each solder joint 16 is formed from a solder preform 92 that is placed between a corresponding feedthrough conductive pathway 26 and a corresponding filter array conductive pathway 36, and then melted to form solder joint 16. FIGS. 7A-7C show an example of the process that may be undertaken to form solder joints 16. FIGS. 7A-7C generally show the components of feedthrough assembly 10 along the same cross-section as in FIG. 6. In some examples, solder joint 16 may be formed from a solder ball grid array or solder paste.

As shown in FIG. 7A, feedthrough 12 and filter array 14 may initially be separate and unattached, but may be aligned for attachment, e.g. with one of the plurality of feedthrough conductive pathways 26 being substantially aligned with a corresponding filter array conductive pathway 36. Solder preform 92 may be positioned between feedthrough conductive pathway 26 and the corresponding filter array conductive pathway 36 in the desired alignment. In some examples, solder preform 92 may comprise alignment portion 94 that mates with a portion of either feedthrough 12 or filter array 14 so that solder preform 92 self-aligns with the corresponding feedthrough conductive pathway 26 or the corresponding filter array conductive pathway 36, or both. In one example, shown in FIG. 7A, wherein feedthrough conductive pathway 26 comprises a via 54 with contact pads 56, 58 on either end of via 54 and filter array conductive pathway 36 comprises a via 74 comprising a termination plug that substantially fills only a portion of via hole 76, a portion of via hole 76 proximate externally-facing side 34 is open, e.g., not filled with termination plug 74, to form a recess. In this example, alignment portion 94 comprises a stem of solder preform 92 that may be inserted or otherwise mated into the vacant axial portion of via hole 76. As shown in FIGS. 7A and 7B, stem 94 may be configured so that stem 94 substantially fills the vacant portion of via hole 76, and in particular so that after solder joint 16 is formed, the vacant portion of via hole 76 is substantially filled with solder joint 16. In some examples, termination plug 74 may substantially fill all of via 74. Similar configuration may be used with other examples electrically conductive members described herein.

In other examples, the alignment portion of solder preform 92 may provide for alignment of solder preform 92 with a portion of feedthrough 12, such as an unfilled portion of via 54 (not shown). Alternatively, solder preform 92 may comprise more than one alignment portion, such as alignment portion 94 that is inserted into a portion of filter array to provide self-alignment of solder preform 92 with filter array conductive pathway 36, and a second alignment portion (e.g., a second stem similar to stem 94) that is inserted into a portion of feedthrough 12 to provide self-alignment of solder preform 92 with feedthrough conductive pathway 26. In another example, described in more detail below, a fixture may be used to align feedthrough 12 and filter array 14 with respect to one another so that, if solder preform 92 is substantially aligned with either feedthrough 12 or filter array 14, such as with alignment portion 94, then solder preform 92 will be substantially aligned with the other of feedthrough 12 and filter array 14.

Solder preform 92 may also comprises a portion that is configured to provide for electrical and mechanical coupling between a contact pad and solder joint 16. In one example, shown best in FIG. 7A, solder preform 92 comprises a surface 96 that is configured to provide a bond to a corresponding inwardly-facing contact pad 56 of feedthrough 12. Surface 96 has a surface area that is approximately equal to, or slightly smaller than, the surface area of contact pad 56. In some examples, surface 96 has a geometry that is complimentary to the geometry of contact pad 56, for example, if contact pad 56 has a generally rectangular or square shape (as in FIG. 3), than surface 96 of solder preform 92 may have a similar generally rectangular or square shape. In one example, both contact pad 56 and surface 96 are substantially planar so that surface 96 may be abutted against contact pad 56 so that substantially the entire area of surface 96 is in contact with contact pad 56.

FIG. 7B shows the configuration of the respective components after solder preform 92 has been positioned between feedthrough conductive pathway 26 and filter array conductive pathway 36, and after solder preform 92 has been oriented properly, e.g., so that alignment portion 94 is directed toward the vacant portion of via hole 76, and after feedthrough 12 and filter array 14 have been moved together so that solder preform 92 is sandwiched between feedthrough conductive pathway 26 and filter array conductive pathway 36. In some examples, an alignment portion 94 of solder preform 92 may be inserted into a corresponding opening in either feedthrough 12 or filter array 14, such as via hole 76, before bringing feedthrough 12 and filter array 14 together.

FIG. 7C shows the configuration of the respective components after an example solder joint 16 has been formed, e.g., by melting solder preform 92. In one example, solder joints 16 are formed by raising the temperature of solder preforms 92 above the melting temperature of the material or materials that form solder preform 92. As shown in FIG. 7C, solder preform 92 melts so that the solder material reflows to substantially fill the entirety of via hole 76 that had not been filled by termination plug 74. In one example, the spacing between feedthrough 12 and filter array 14 decreases slightly as the solder material of solder preform 92 reflows to form solder joint 16, as shown in FIGS. 7B and 7C. In one example, the solder material of solder preform 92/solder joint 16 substantially wets substantially the entire inner surface of via hole 76 and substantially the entire outwardly-facing surface of termination plug 74 to provide adequate electrical coupling between solder joint 16 and the corresponding filter array conductive pathway 36, and to provide adequate mechanical coupling between solder joint 16 and filter array 14. In one example, the solder material of solder preform 92/solder joint 16 substantially wets a majority of the inwardly-facing surface of contact pad 56 and, in one example, substantially completely wets the portion of contact-pad 56 that is covered/wetted by solder joint 16, to ensure adequate mechanical and electrical coupling between the corresponding feedthrough conductive pathway 26 and solder joint 16.

As noted above, in some examples, the melting temperature of solder preforms is between about 150° C. and about 350° C. In one example, the melting temperature of solder preforms 92 is below temperatures that may adversely affect feedthrough 12 or filter array 14. For example, capacitive filters 38 may be particularly sensitive to high rises in temperature, because the high temperatures may produce mechanical stress on capacitive filters 38 due to mismatches in thermal coefficients of expansion of capacitive filters 38 and surrounding materials. However, because solder preform 92 may be selected to have a relatively low melting temperature, the risk of damage to capacitive filters 38 is reduced or eliminated.

Figure 8:
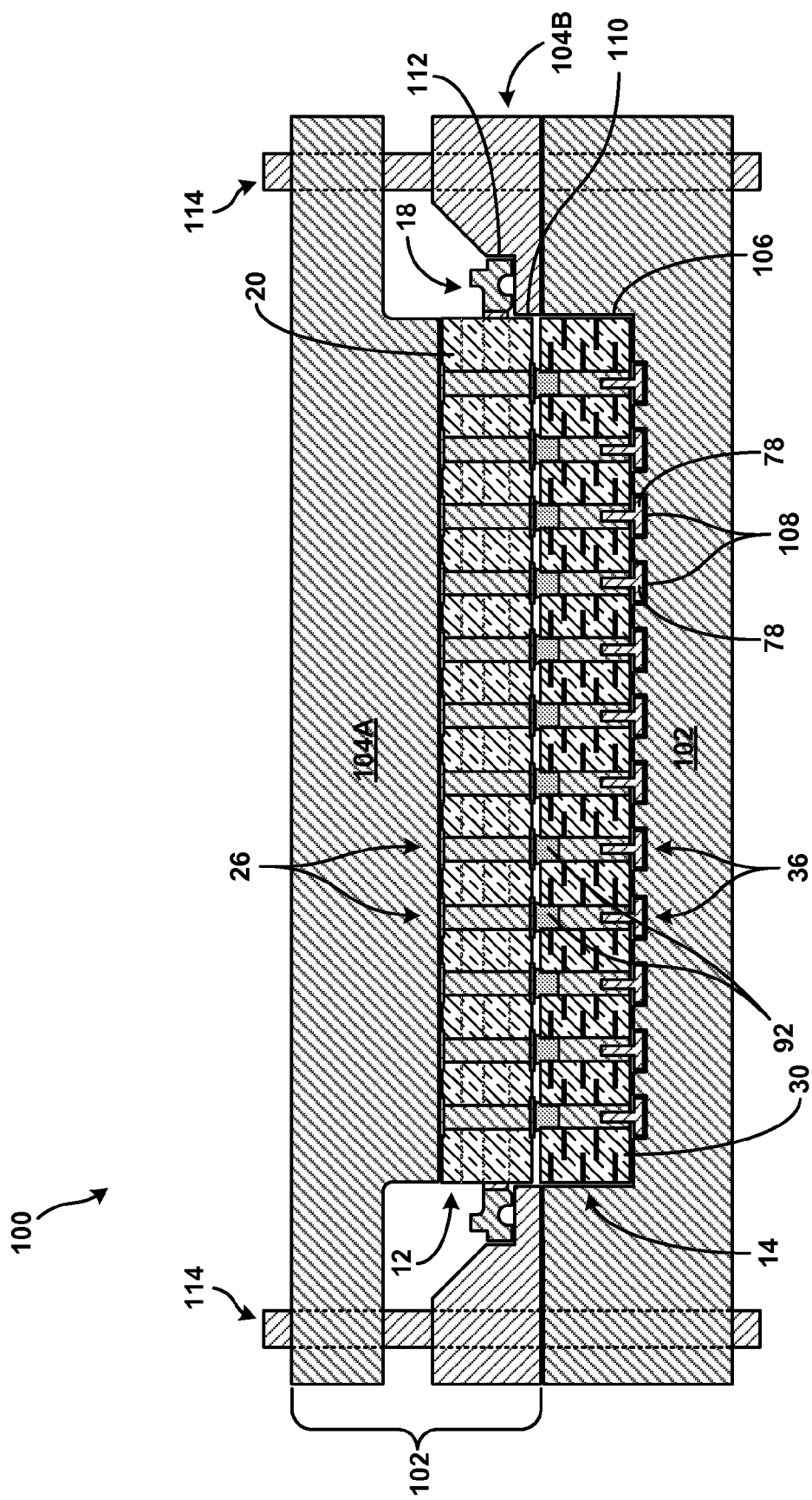
FIG. 8 is a cross-sectional view illustrating of an example fixture that may be used to attach the example feedthrough to the example filter array.

In one example, one or more fixtures may be used to hold feedthrough 12 and filter array 14 in place. FIG. 8 illustrates a cross-sectional view (taken generally along the same cross section as shown above in FIG. 5) of an example fixture 100 for holding feedthrough 12 and filter array 14 in place during the melting of solder preforms 92 to form solder joints 16. In the example shown in FIG. 8, fixture 100 comprises a feedthrough portion 102 and a filter array portion 104. Filter array portion 102 is oriented to be below feedthrough portion 104 in the example of FIG. 8, but the orientation could be reversed.

Filter array 14 is placed within a compartment 110 within filter array portion 102 of fixture 100. Compartment 110 is configured so that filter array 14 does not move laterally with respect to filter array portion 102 of fixture 100. Filter array portion 102 may also comprise a plurality of pockets 108 that are configured to fit lead frames 78 therein to further secure filter array 14 and to further prevent movement of filter array 14 with respect to filter array portion 102 of fixture 100.

Feedthrough portion 104 comprises an upper portion 104A and a lower portion 104B. Feedthrough 12 fits within an opening 110 in lower portion 104B, wherein opening 110 has a cross-sectional shape that is substantially the same as that of feedthrough 12, only slightly larger, so that when feedthrough 12 is fitted within opening 206, feedthrough substrate 20 is prevented from moving laterally with respect to lower portion 104B. In one example, lower portion 104B comprises a pocket 112, wherein ferrule 18 fits within pocket 112. Pocket 12 may be is configured to have a cross-sectional shape that corresponds to the shape of ferrule 18, only slightly larger, to further secure feedthrough 12 and ferrule 18 and prevent their movement with respect to lower portion 104B. As can be seen in FIG. 8, opening 110 of lower portion 104B may be substantially aligned with compartment 106 of filter array portion 102 so that feedthrough 12 is substantially aligned with filter array 14, which in turn substantially aligns feedthrough conductive pathways 26 with filter array conductive pathways 36.

Upper portion 104A is placed on top of feedthrough substrate 20 in order to provide a downward pressure, e.g., due to the weight of upper portion 104A, which may help to ensure the formation of electrical and mechanical coupling between solder joints 16 and feedthrough conductive pathways 26 and conductive pathways 36 of filter array 36, as described above.

Filter array portion 102 and feedthrough portion 104 are substantially aligned so that each feedthrough conductive pathway 26 is substantially aligned with a corresponding solder preform 92 and is also substantially aligned with a corresponding conductive pathway 36 of filter array 30 to provide for a resulting solder joint 16 that is in a desired position between the conductive pathways 26, 36. Fixture 100 may comprise a mechanism that ensures that filter array portion 102 and feedthrough portion 104 as substantially aligned, which in turn ensures that filter array 14 and feedthrough 12 and conductive pathways 26, 36 are substantially aligned. In one example, the alignment mechanism comprises two or more posts 114 that extend through aligned holes within filter array portion 102, upper portion 104A, and lower portion 104B. Posts 114 act to align filter array portion 102, upper portion 104A, and lower portion 104B in a desired relative orientation. Posts 114 also act to prevent filter array portion 102, upper portion 104A, and lower portion 104B from moving laterally with respect to one another after filter array portion 102, upper portion 104A, and lower portion 104B have been aligned so that feedthrough 12 and filter array 14, and hence conductive pathways 26, 36 remain substantially aligned while melting solder preforms 92 to form solder joints 16.

Returning to FIG. 6, as noted above, each capacitive filter 38 of filter array 14 may comprise a plurality of active electrodes 86 that are electrically coupled to a corresponding conductive pathway 36 of capacitive filter 38 and a plurality of ground electrodes 84. Ground electrodes 84 may be connected to ferrule 18 using ground fingers 120 (also referred to as spring contacts) through termination 90. Ground fingers 120 may be laser welded to ferrule 18 at location 218. Ground electrodes 86 may also be electrically coupled to a termination 90, for example at a lateral exterior of filter array 14. Termination 90 may extend substantially along the entire length of filter array 14 on either side of filter array 14, as shown in FIG. 3, so that each ground electrode 84 is electrically coupled to a corresponding termination 90. Each termination 90 is electrically coupled to a common ground so that the EMI signals being filtered by filter array 14 is grounded. In one example, shown in FIG. 6, termination 90 is grounded by being electrically coupled to ferrule 18, which in turn is electrically coupled to the IMD housing.

In the example shown in FIG. 6, a pair of ground fingers 120 are each electrically coupled to a corresponding termination 90 at one end and are electrically coupled to ferrule 18 and the other end. In one example, each ground finger 120 comprises a tab 122 that is inserted into a corresponding groove 124 in ferrule 18. A solder joint 126 may be formed between tab 122 and groove 124 to ensure electrical coupling. Additionally or alternatively, ground finger 120 may be laser welded at location 218 to ferrule 18, and groove 124 and tab 122 may provided for alignment of ground fingers 120 and ferrule 18 when assembled. In some examples, ground finger 120 and ferrule 18 may be a single integral piece.

Ground finger 120 may also comprise a finger tip 128 that forms an electrical connection with a corresponding termination 90. In one example, ground fingers 120 comprise a resilient material that is configured to provide a pinching force at finger tip 128 wherein the pressure between finger tip 128 and termination 90 provides sufficient electrical contact between ground finger 120 and termination 90. In another example, shown in FIG. 6, a solder joint 130 may be formed between each finger tip 128 and a corresponding termination 90, such as within a groove 132 within termination 90. In some examples, a solder joint may be formed between ground fingers 120 and filter capacitor 14 at location 220. Additionally or alternatively, assembly 10 may rely entirely on ground fingers 120 for making the capacitor to ground connection, instead of using solder. In such a case, solder may be for added redundancy.

Figure 9:
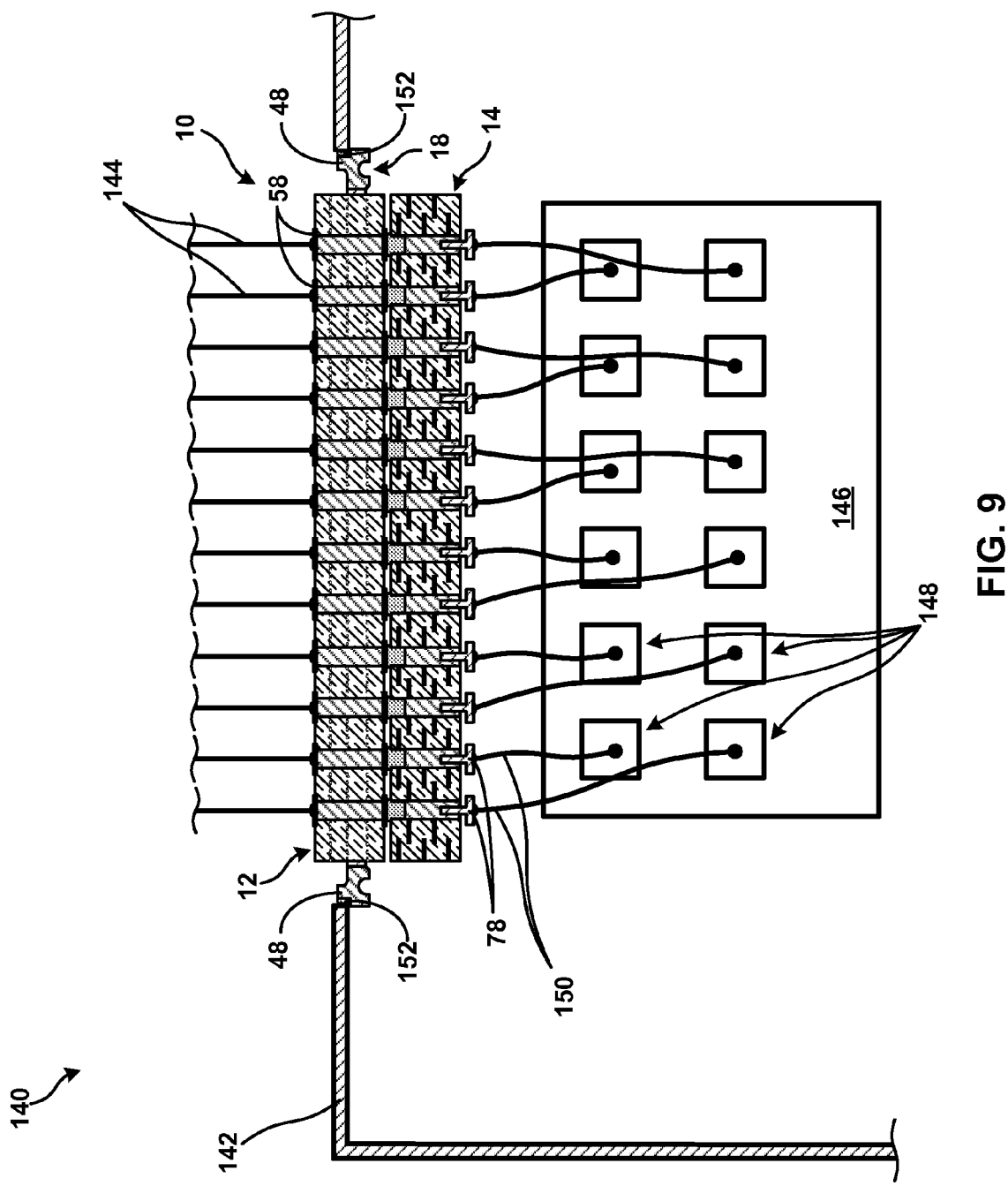
FIG. 9 is a conceptual diagram illustrating the example feedthrough assembly of FIG. 1 mounted within an opening of an example implantable medical device.

FIG. 9 is a conceptual diagram showing feedthrough assembly 10 mounted within a housing 142 of an electronics device 140, such as an implantable medical device 140. In some examples, IMD 140 provides for electrical stimulation of a target tissue via a plurality of lead conductors 144 which are electrically coupled to a plurality of electrodes (not shown), or IMD 140 senses bioelectric signals that are picked up by the electrodes and transmitted back to IMD 140 by lead conductors 144, or both. IMD 140 further comprises electronics 146 (shown conceptually in FIG. 9) enclosed within housing 142, which may be in the form of a printed wiring board. Electronics 146 may comprise a plurality of contact pads 148 that provide a surface for bonding a conductor, such as a wire 150, which in turn is bonded to a corresponding filter array conductive pathway 36, such as by being bonded to a corresponding lead frame 78. Lead conductors 144 are each bonded to a corresponding feedthrough conductive pathway 26, such as by being bonded to a corresponding contact pad 58.

Ferrule 18 is mounted in an opening of housing 142 of IMD 140. In one example, a hermetic seal is formed between ferrule 18 and housing 142, such as with a weld 152. In the example shown in FIG. 9, weld 152 is formed between mounting flange 48 of ferrule 18 and the edge of the opening in housing 142. Weld 152 may comprise a material that is compatible with the material of housing 142 and the material of ferrule 18. As described above, in some examples, ferrule 18 may comprise titanium or a titanium alloy, and housing 142 may also comprise a titanium or titanium alloy. In such an example, weld 152 provides for a hermetic seal between the titanium or titanium alloy of ferrule 18 and the titanium or titanium alloy of housing 142. In some examples, weld 152 is formed using a laser welding process, e.g., to form a Ti—Ti weld.

Figure 10:
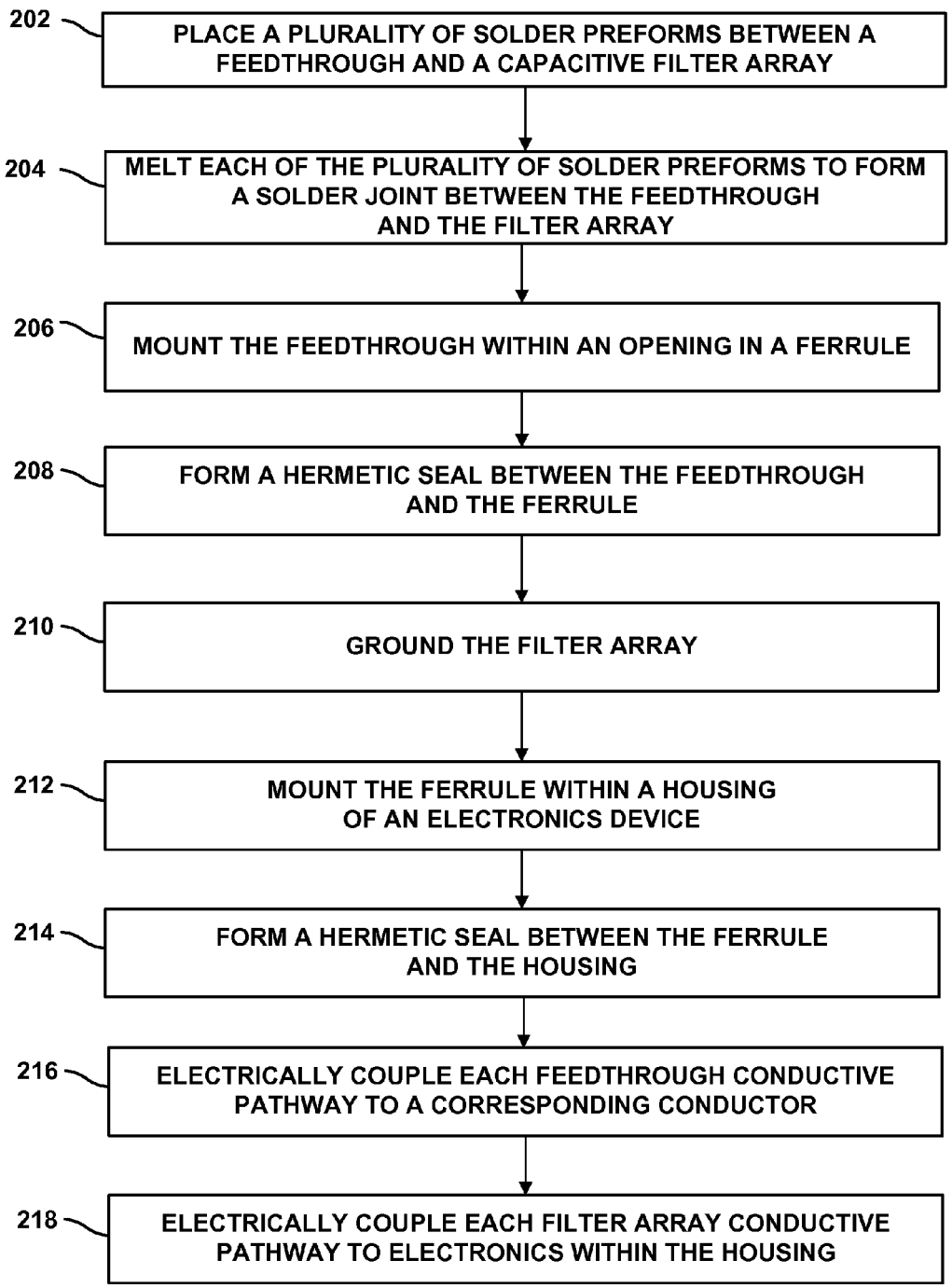
FIG. 10 is a flowchart illustrating an example method of attaching the example feedthrough to the example filter array.

FIG. 10 is a flow diagram illustrating an example technique for forming a feedthrough assembly, such as feedthrough assembly 10, and then incorporating the feedthrough assembly into an electronics device, such as, IMD 140. For ease of illustration, the technique of FIG. 10 is described with regard to feedthrough assembly 10. The example technique of FIG. 10 includes forming a plurality of solder joints 16 between a feedthrough 12 and a capacitive filter array 14, wherein each of solder joints 16 is formed between a corresponding one of a plurality of feedthrough conductive pathways 26 and a corresponding one of a plurality of filter array conductive pathways 36 to mechanically couple and electrically couple the corresponding one of the plurality of feedthrough conductive pathways 26 to the corresponding one of the plurality of filter array conductive pathways 36. As shown in FIG. 10, the example technique includes placing a plurality of solder preforms 92 between a feedthrough 12 and a capacitive filter array 14, wherein each of the plurality of solder preforms 92 is placed between a corresponding one of a plurality of conductive pathways 26 of the feedthrough 12 and a corresponding one of a plurality of filter array conductive pathways 36 (202). The example technique further comprises melting each of the plurality of solder preforms 92 to form a solder joints 16 between the corresponding one of the plurality of feedthrough conductive pathways 26 and the corresponding one of the plurality of filter array conductive pathways 36 to form a solder joint 16 (204), wherein each solder joint 16 mechanically couples and electrically couples the corresponding one of the plurality of feedthrough conductive pathways 26 to the corresponding one of the plurality of filter array conductive pathways 36.

The example technique of FIG. 10 may also comprise mounting feedthrough 12 within an opening 46 in a ferrule 18 (206) and forming a hermetic seal 50 between feedthrough 12 and ferrule 18 (208), such as by forming a braze joint 52 between feedthrough 12 and ferrule 18. The example technique may also include grounding filter array 14 (210) so that EMI that is filtered by capacitive filters 38 of filter array 14 is grounded, such as by electrically coupling a ground termination 90 of filter array 14 to ferrule 18, which in turn is electrically coupled to a housing of the electronics device. The technique of FIG. 10 may also comprise mounting ferrule 18 within a housing of an electronics device (212), such as housing 142 of IMD 140, and forming a hermetic seal between ferrule 18 and housing 142 (214), such as by forming a weld 152 between ferrule 18 and housing 142. The method may also comprise electrically coupling each feedthrough conductive pathway 26 to a corresponding conductor (216), such as lead conductor 144 and electrically coupling each filter array conductive pathway 36 to electronics 146 within housing 142 (218).

Figure 11:
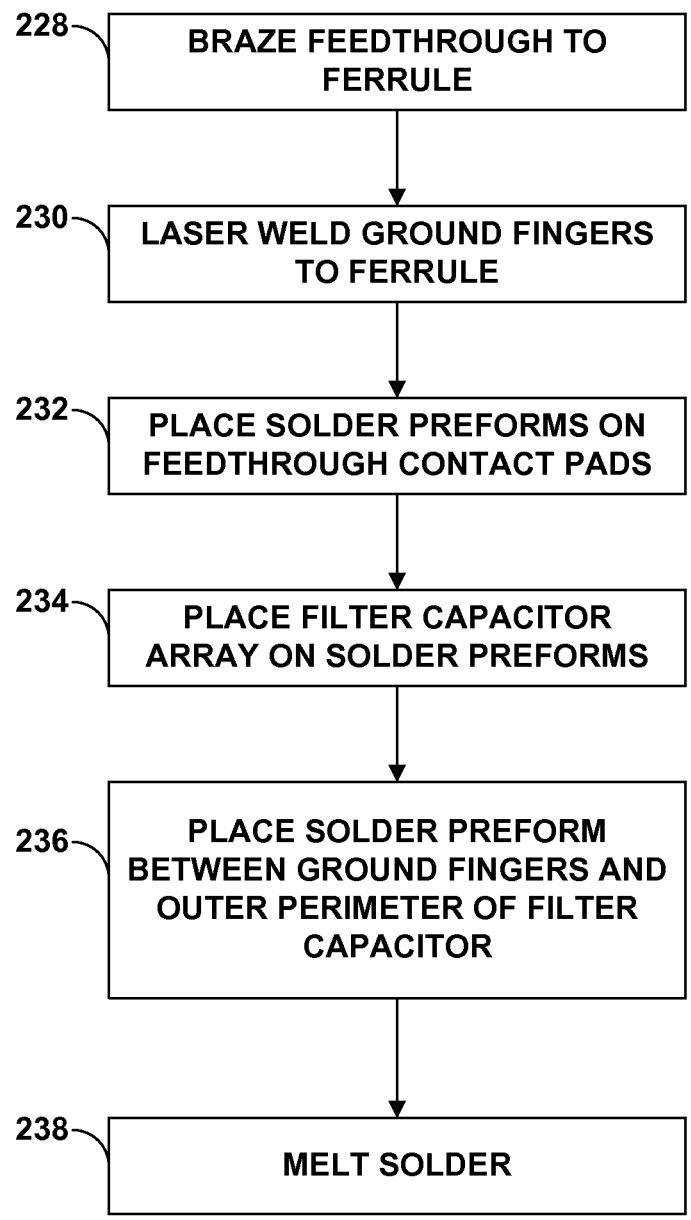
FIG. 11 is a flow diagram illustrating another example technique for assembling an example feedthrough assembly.

FIG. 11 is a flow diagram illustrating another example technique for assembling an example feedthrough assembly, such as, e.g., feedthrough assembly 10. As shown in FIG. 11, feedthrough 12 may be secured within opening 46 in ferrule 18 by forming braze joint 52 (228). Ground fingers 120 may then be laser welded to ferrule 18, e.g., at location 218 (230). Solder preforms 16 may then be placed on feedthrough contact pads 56 (232). Capacitive filter array 14 may then be placed on solder preforms 16, e.g., in the configuration shown in FIG. 7B (234). Solder preforms may then be placed at location 220 (FIG. 6) between ground fingers 120 and the outer diameter of capacitive filter array 14 (236). The assembly may then be heated to melt the solder of solder preforms 16 and that solder placed at location 220 (238). In this manner, ferrule 18, ground fingers 120, feedthrough array 12, and capacitive filter array 14 may be mechanically coupled to each other via solder preforms 16 and the solder joint formed at location 220. Furthermore, the solder joint formed by melting solder preforms 16 may electrically couple conductive pathways 36 and 26, as described above.

Figure 12:
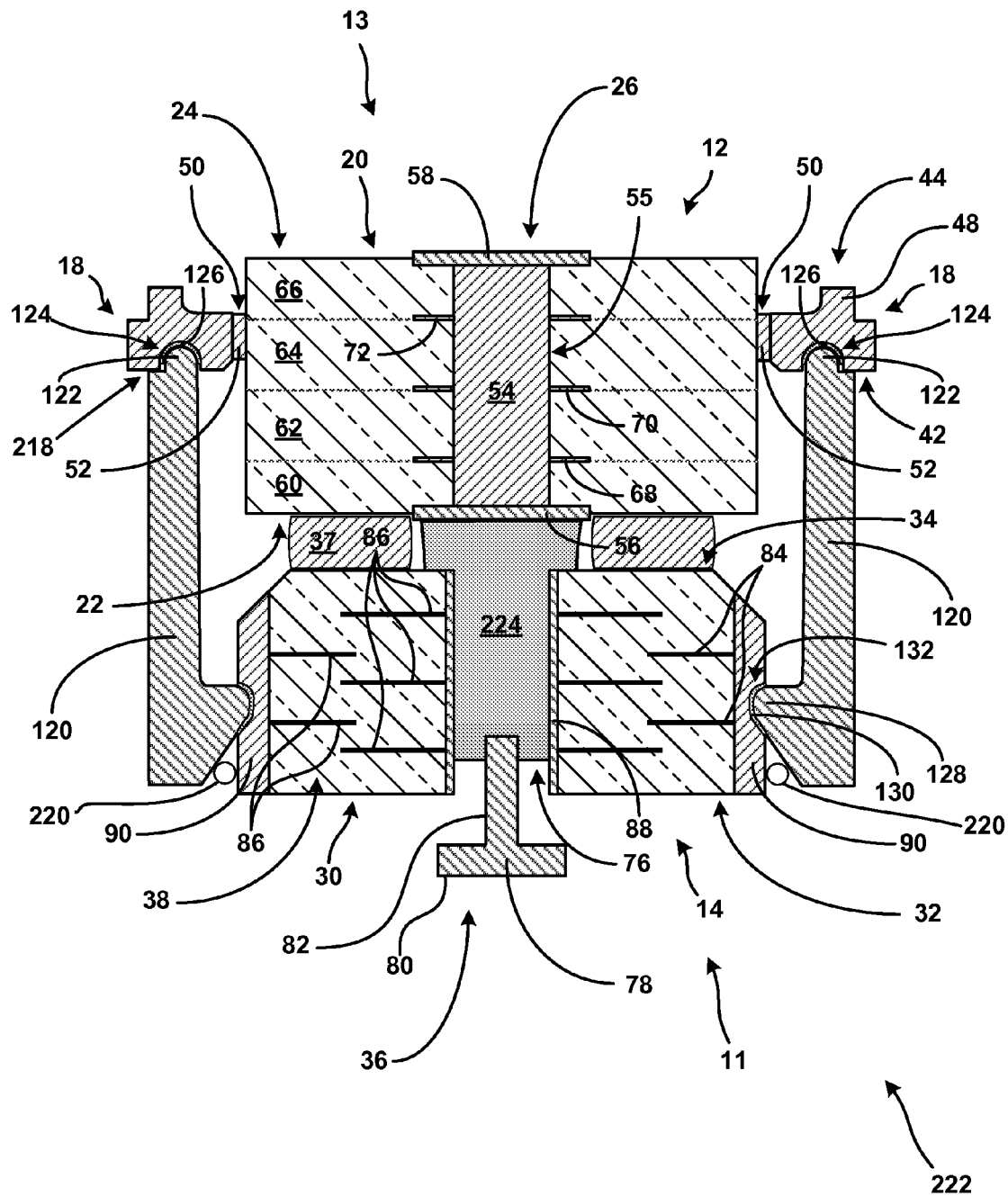
FIG. 12 is a conceptual diagram illustrating another example feedthrough assembly.

FIG. 12 is a conceptual diagram illustrating another example feedthrough assembly 222. Feedthrough assembly 222 is substantially the same or similar to that of assembly 10 shown, for example, in FIG. 6, and similar features are similarly numbered and named. However, unlike that of assembly 10, assembly 222 does not include solder joint 16 as an electrically conductive member. As noted above, electrically conductive members other than that of solder perform/solder joints may be used to electrically couple conductive pathway 26 of feedthrough 12 to conductive pathway 36 of capacitive filter array 36. In the example of FIG. 12, assembly 222 includes an electrically conductive member in the form of a solder joint formed by cylindrical shaped perform 224 located partially within via 76. As shown, solder joint formed by cylindrical shaped perform 224 directly couples (electrically) lead frame 78 to pad 56.

Figure 13:
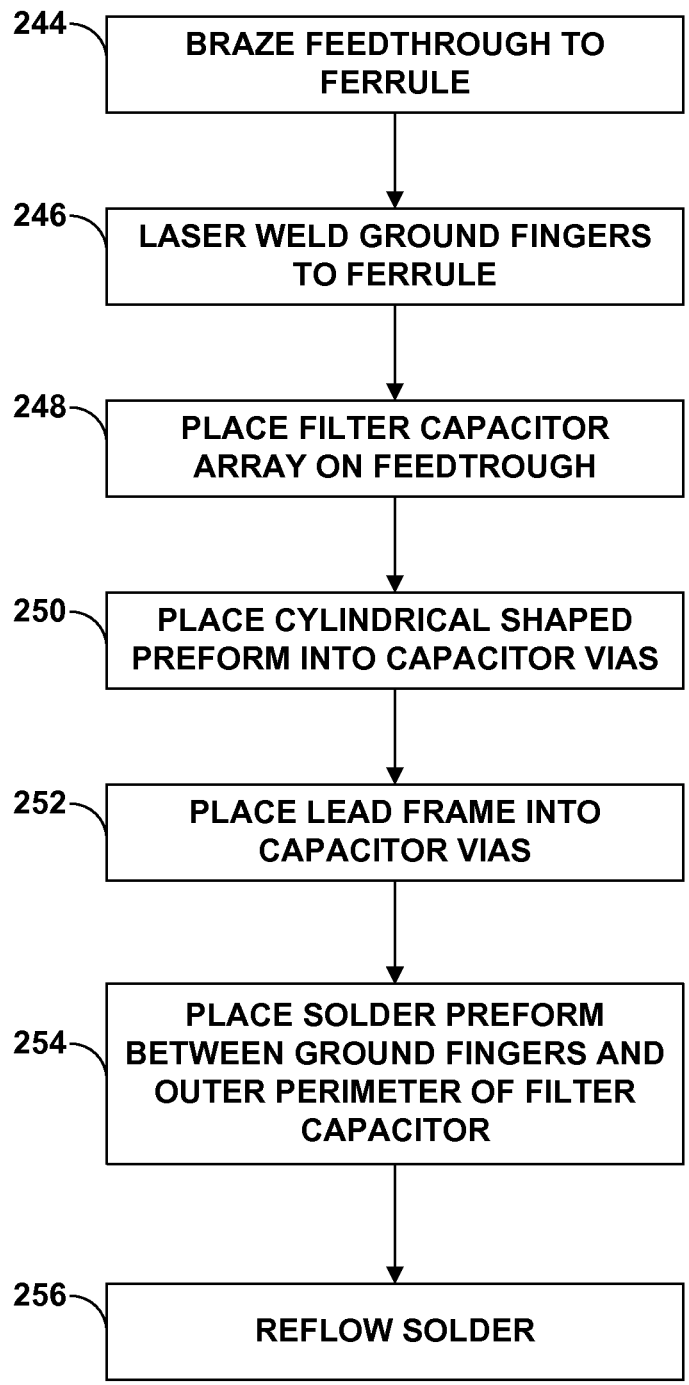
FIG. 13 is a flow diagram illustrating an example technique for assembling the feedthrough assembly of FIG. 12.

FIG. 13 is a flow diagram illustrating an example technique for assembling the feedthrough assembly of FIG. 12. As shown in FIG. 12, feedthrough 12 may be secured within opening 46 in ferrule 18 by forming braze joint 52 (244). Ground fingers 120 may then be laser welded to ferrule 18, e.g., at location 218 (246). Subsequently, capacitive filter array 14 may be place on feedthrough 12 (248). Cylindrical solder performs 224 may then be placed into respective capacitor vias 76 (250). Lead frames 76 may then be place into capacitor vias 76 with cylindrical solder performs 224 (252). Solder preforms may then be placed at location 220 (FIG. 6) between ground fingers 120 and the outer diameter of capacitive filter array 14 (254). The assembly may then be heated to melt or reflow the solder of solder preforms 224 and that solder placed at location 220 (256). In this manner, ferrule 18, ground fingers 120, feedthrough array 12, and capacitive filter array 14 may be mechanically coupled to each other via solder performs 224 and/or the solder joint formed at location 220. Furthermore, the solder joint formed by melting solder preforms 224 may electrically couple conductive pathways 36 and 26, as described above.

Figure 14:
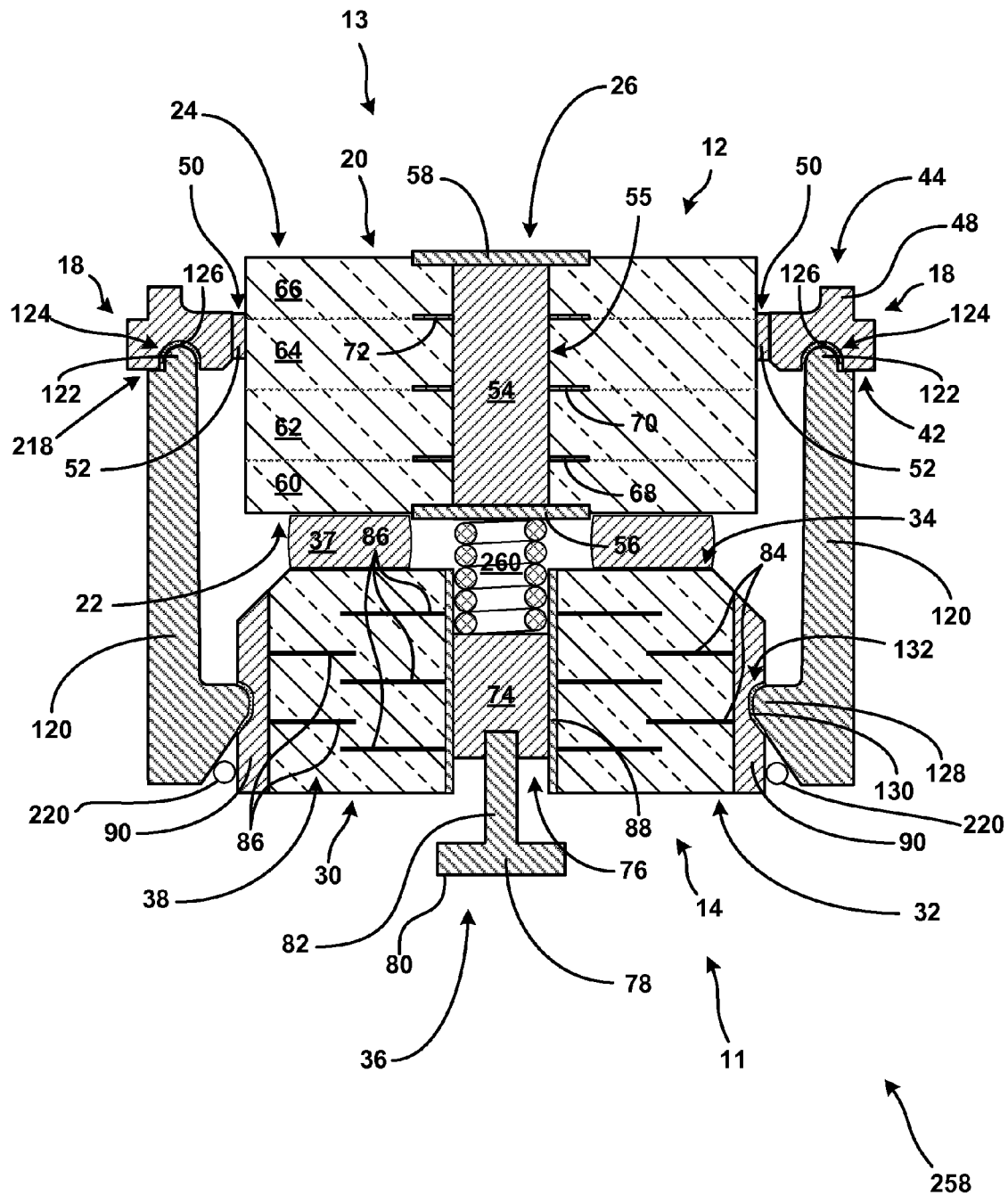
FIG. 14 is a conceptual diagram illustrating another example feedthrough assembly.

FIG. 14 is a conceptual diagram illustrating another example feedthrough assembly 258. Feedthrough assembly 258 is substantially the same or similar to that of assembly 10 shown, for example, in FIG. 6, and similar features are similarly numbered and named. However, unlike that of assembly 10, assembly 258 does not include solder joint 16 as an electrically conductive member. As noted above, electrically conductive members other than that of solder perform/solder joints may be used to electrically couple conductive pathway 26 of feedthrough 12 to conductive pathway 36 of capacitive filter array 36. For example, an electrically conductive member may be formed by coiled spring connectors, spring-loaded contact connectors (e.g., single or double pogo connectors), or other pressure contacts, conductive epoxies/polymers, scraping contacts, fuzz button interconnects, and the like.

In the example of FIG. 14, assembly 258 includes an electrically conductive member in the form of coiled spring 260 formed from an electrical conductive material, such as, copper (Cu), silver (Ag), gold (Au), platinum (Pt), or other suitable material. One end of spring 260 is in contact with inwardly-facing contact pad 56 of feedthrough 12 while the other end of spring 260 is in contact with via 74. In such a configuration, conductive pathway 26 of feedthrough 12 may be electrically coupled to conductive pathway 36 of filter array 14 via spring 260 to allow for conduction of an electrical signal through filter assembly 258. In some examples, spring 260 may be biased such that a pressure contact is formed against the points of contact with contact pad 56 and via 74 to ensure electrical coupling is maintained over time.

Unlike that of solder joint 16 (FIG. 6), spring 260 may not provide for mechanical coupling of feedthrough 12 to filter array 14. Instead, other techniques for mechanical coupling may be used to attach feedthrough 12 to filter array 14. As described above, in some examples, such mechanical coupling may be accomplished via solder joints at location 220 to attach ground fingers 120 to filter array 14, which in turn mechanically couples filter array 14 to feedthrough 12 by way of ferrule 18. When assembling assembly 258, pressure may be applied during the melting process of solder at location 220 to counterattack the bias of spring 260 until the solder joint is formed to provide for mechanical coupling of assembly 258.

Figure 15:
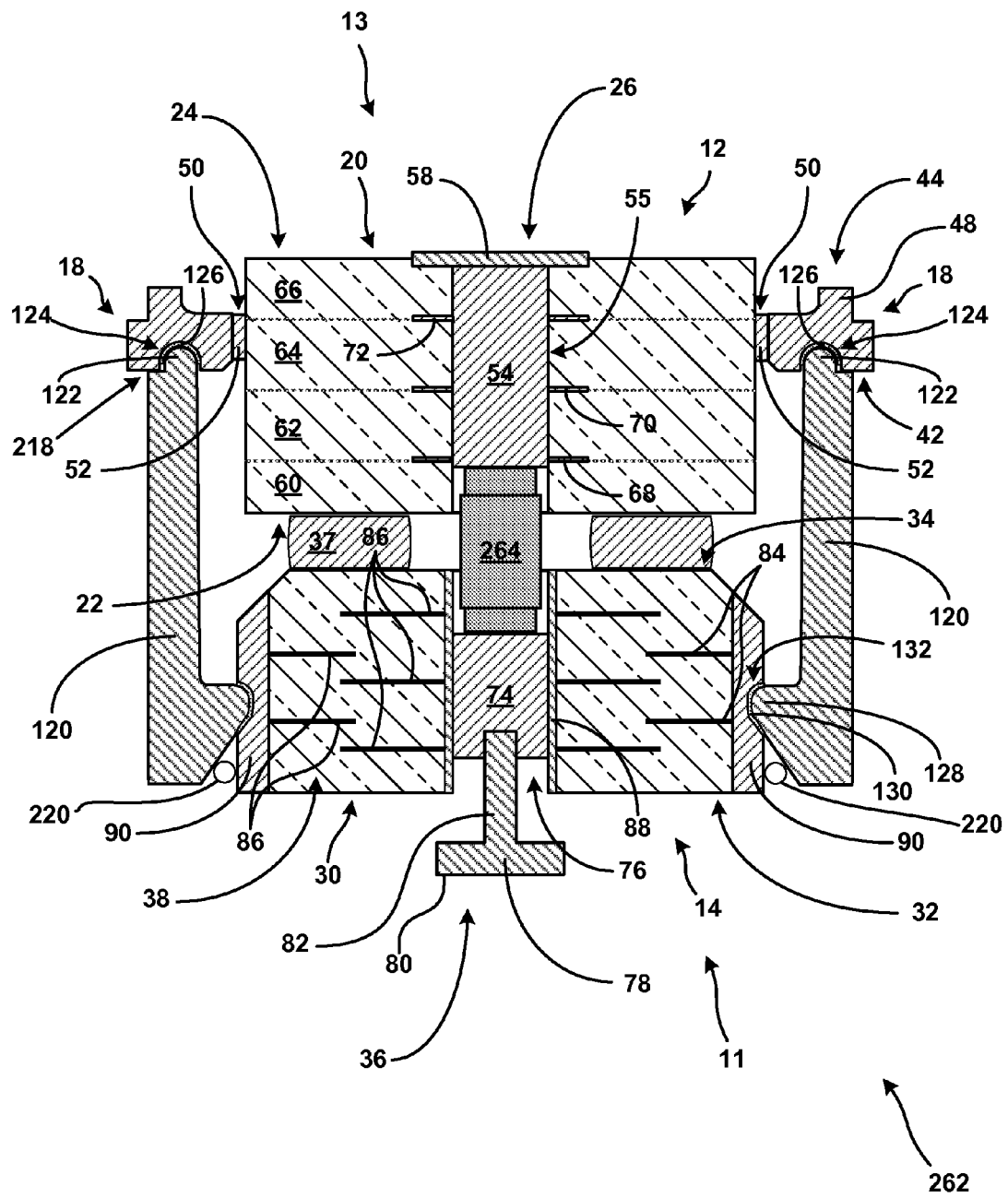
FIG. 15 is a conceptual diagram illustrating another example feedthrough assembly.

FIG. 15 is a conceptual diagram illustrating another example feedthrough assembly 262. Feedthrough assembly 262 is substantially the same or similar to that of assembly 258 shown, for example, in FIG. 14, and similar features are similarly numbered and named. However, unlike that of assembly 258, assembly 262 does not include coiled spring 262 as an electrically conductive member. Instead, assembly 262 includes spring-loaded contact connector 264. Contact connector 264 is shown as a double pogo connector, but other suitable connectors such as, e.g., a single pogo connector may be used. Moreover, other suitable electrically conductive member may be used, such as, e.g., other pressure contacts, conductive epoxies/polymers, scraping contacts, fuzz button interconnects, and the like.

Similar to that of spring 260, one end of connector 264 is in contact with inwardly-facing contact pad 56 of feedthrough 12 while the other end of connector 264 is in contact with via 74. In such a configuration, conductive pathway 26 of feedthrough 12 may be electrically coupled to conductive pathway 36 of filter array 14 via connector 264 to allow for conduction of an electrical signal through filter assembly 258. In some examples, due to the spring loaded design, connector 264 may be biased such that a pressure contact is formed against the points of contact with contact pad 56 and via 74 to ensure electrical coupling is maintained over time.

Unlike that of solder joint 16 (FIG. 6), connector 264 may not provide for mechanical coupling of feedthrough 12 to filter array 14. Instead, other techniques for mechanical coupling may be used to attach feedthrough 12 to filter array 14, including those described above with regard to FIG. 14, for example. Again, when assembling assembly 262, pressure may be applied during the melting process of solder at location 220 to counterattack the bias of connector 264 until the solder joint is formed to provide for mechanical coupling of assembly 258.

Various embodiments of the invention have been described. These and other embodiments are within the scope of the following claims.

The invention claimed is:

1. A filtered feedthrough assembly comprising:
   a feedthrough comprising at least one feedthrough conductive pathway extending between a first feedthrough side and a second feedthrough side;
   a capacitive filter array comprising at least one filter array conductive pathway extending between a first filter array side and a second filter array side, and at least one capacitor filter of the capacitor filter array substantially surrounding at least a portion of the at least one filter array conductive pathway, wherein the at least one filter array conductive pathway comprises a termination plug including an electrically conductive material substantially filling a portion of a via extending between the first filter array side and the second filter array side; and
   at least one electrically conductive member electrically coupling the at least one filter array conductive pathway to the at least one feedthrough conductive pathway, wherein the at least one electrically conductive member comprises an alignment portion configured to mate with the via so as to align the at least one feedthrough conductive pathway with the at least one filter array conductive pathway.

2. The filtered feedthrough assembly of claim 1, wherein the at least one electrically conductive member comprises at least one solder joint mechanically coupling and electrically coupling the at least one filter array conductive pathway to the at least one feedthrough conductive pathway.

3. The filtered feedthrough assembly of claim 2, wherein the at least one solder joint comprises at least one of an indium-silver alloy, a tin-silver alloy, tin-copper alloy, tin-silver-copper alloy, tin-lead alloy, and gold-tin alloy.

4. The filtered feedthrough assembly of claim 2, wherein the at least one solder joint is formed by melting a solder preform.

5. The filtered feedthrough assembly of claim 1, wherein:
the at least one feedthrough conductive pathway comprises a plurality of feedthrough conductive pathways extending between the first feedthrough side and the second feedthrough side;
the at least one filter array conductive pathway comprises a plurality of filter array conductive pathways extending between the first array side and the second array side, the at least one capacitive filter comprises a plurality of capacitor filters each substantially surrounding at least a portion of a corresponding one of the plurality of filter array conductive pathways; and
the at least one electrically conductive member comprises a plurality of electrically conductive members, each electrically conductive member electrically coupling one of the plurality of filter array conductive pathways to a corresponding one of the plurality of feedthrough conductive pathways.

6. The filtered feedthrough assembly of claim 1, wherein the at least one electrically conductive member comprises at least one of a coiled spring connector, spring-loaded contact connector, conductive epoxy, conductive polymer, scraping contact, or fuzz button interconnect.

7. The filtered feedthrough assembly of claim 1, wherein the termination plug comprises at least one of silver, palladium, platinum, gold, nickel, and alloys thereof.

8. The filtered feedthrough assembly of claim 1, wherein the at least one feedthrough conductive pathway comprises a second via and a connection pad electrically coupled to the second via at the first feedthrough side, wherein the at least one electrically conductive member is bonded to the connection pad.

9. The filtered feedthrough assembly of claim 1, further comprising a ferrule defining a ferrule opening, wherein the feedthrough extends through the ferrule opening and a hermetic seal is formed between the feedthrough and the ferrule.

10. The filtered feedthrough assembly of claim 1, wherein the feedthrough comprises a cofired ceramic substrate.

11. The filtered feedthrough assembly of claim 10, wherein the cofired ceramic substrate comprises a high-temperature cofired ceramic (HTCC) material.

12. An implantable medical device comprising:
a housing;
electronics enclosed within the housing;
a ferrule mounted within an opening in the housing, the ferrule comprising a ferrule opening extending between an internally-facing ferrule side and an externally-facing ferrule side;
a feedthrough mounted in the ferrule opening, wherein a hermetic seal is formed between the feedthrough and the ferrule, the feedthrough comprising at least one feedthrough conductive pathway extending through the feedthrough between an internally-facing feedthrough side and an externally-facing feedthrough side;
a capacitive filter array comprising at least one filter array conductive pathway extending between an internally-facing filter array side and an externally-facing filter array side, and at least one capacitor filter of the capacitive filter array substantially surrounding at least a portion of the at least one filter array conductive pathway;
at least one electrically conductive member electrically coupling the at least one filter array conductive pathway to the at least one feedthrough conductive pathway, wherein the at least one electrically conductive member comprises a coiled spring formed of an electrically conductive material.

13. A filtered feedthrough assembly comprising:
a feedthrough comprising at least one feedthrough conductive pathway extending between a first feedthrough side and a second feedthrough side; a capacitive filter array comprising at least one filter array conductive pathway extending between a first filter array side and a second filter array side, and at least one capacitor filter of the capacitor filter array substantially surrounding at least a portion of the at least one filter array conductive pathway; and at least one electrically conductive member electrically coupling the at least one filter array conductive pathway to the at least one feedthrough conductive pathway, wherein the at least one electrically conductive member comprises a coiled spring formed of an electrically conductive material.

14. An implantable medical device comprising:
a housing;
electronics enclosed within the housing;
a ferrule mounted within an opening in the housing, the ferrule comprising a ferrule opening extending between an internally-facing ferrule side and an externally-facing ferrule side;
a feedthrough mounted in the ferrule opening, wherein a hermetic seal is formed between the feedthrough and the ferrule, the feedthrough comprising at least one feedthrough conductive pathway extending through the feedthrough between an internally-facing feedthrough side and an externally-facing feedthrough side;
a capacitive filter array comprising at least one filter array conductive pathway extending between an internally-facing filter array side and an externally-facing filter array side, at least one capacitor filter of the capacitive filter array substantially surrounding at least a portion of the at least one filter array conductive pathway, wherein the at least one filter array conductive pathway comprises a termination plug including an electrically conductive material substantially filling a portion of a via extending between the internally-facing filter array side and the externally-facing filter array side;
at least one electrically conductive member electrically coupling the at least one filter array conductive pathway to the at least one feedthrough conductive pathway, wherein the at least one electrically conductive member comprises an alignment portion configured to mate with the via so as to align the at least one feedthrough conductive pathway with the at least one filter array conductive pathway.

15. The implantable medical device of claim 14, wherein the at least one electrically conductive member comprises at least one solder joint mechanically coupling and electrically coupling the at least one filter array conductive pathway to the at least one feedthrough conductive pathway.

16. The implantable medical device of claim 15, wherein the at least one solder joint comprises at least one of an indium-silver alloy, a tin-silver alloy, tin-copper alloy, tin-silver-copper alloy, tin-lead alloy, and gold-tin alloy.

17. The implantable medical device of claim 15, wherein the at least one solder joint is formed by melting a solder preform.

18. The implantable medical device of claim 14, wherein:
the at least one feedthrough conductive pathway comprises a plurality of feedthrough conductive pathways extending between the internally-facing feedthrough side and the externally-facing feedthrough side;
the at least one filter array conductive pathway comprises a plurality of filter array conductive pathways extending between the internally-facing array side and the externally-facing array side, the at least one capacitive filter array comprises a plurality of capacitor filters each substantially surrounding at least a portion of a corresponding one of the plurality of filter array conductive pathways; and
the at least one electrically conductive member comprises a plurality of electrically conductive members, each electrically conductive member electrically coupling one of the plurality of filter array conductive pathways to a corresponding one of the plurality of feedthrough conductive pathways.

19. The implantable medical device of claim 14, wherein the at least one electrically conductive member comprises at least one of a coiled spring connector, spring-loaded contact connector, conductive epoxy, conductive polymer, scraping contact, or fuzz button interconnect.

20. The implantable medical device of claim 14, wherein the termination material of the termination plug comprises at least one of silver, palladium, platinum, gold, nickel, and alloys thereof.

21. The implantable medical device of claim 14, wherein the at least one feedthrough conductive pathway comprises a second via and a connection pad electrically coupled to the second via at the internally-facing feedthrough side, wherein the at least one electrically conductive member is bonded to the connection pad.

22. The implantable medical device of claim 14, wherein the ferrule further comprises a mounting flange, the ferrule configured to be welded to the housing at the mounting flange.

23. The implantable medical device of claim 14, wherein the hermetic seal between the feedthrough and the ferrule comprises a braze joint between the feedthrough and the ferrule.

24. The implantable medical device of claim 14, wherein the feedthrough comprises a cofired ceramic substrate.

25. The implantable medical device of claim 24, wherein the cofired ceramic substrate comprises a high temperature cofired ceramic (HTCC) material.

26. The implantable medical device of claim 14, wherein the capacitive filter array comprises a ceramic capacitive filter substrate, wherein the at least one filter array conductive pathway extends through the ceramic capacitive filter substrate between an internally-facing filter substrate side and a generally opposed externally-facing filter substrate side.

27. A method comprising electrically coupling at least one feedthrough conductive pathway of a feedthrough to at least one filter array conductive pathway of a capacitive filter array via at least one electrically conductive member, wherein the at least one feedthrough conductive pathway extends between a first feedthrough side and a second feedthrough side, and wherein the at least one filter array conductive pathway extends between a first filter array side and a second filter array side, and the capacitive filter array comprises at least one capacitor filter substantially surrounding at least a portion of the at least one filter array conductive pathway, wherein the at least one electrically conductive member comprises a coiled spring formed of an electrically conductive material.

28. The method of claim 27, wherein that at least one electrically conductive member comprises at least one of a coiled spring connector, spring-loaded contact connector, conductive epoxy, conductive polymer, scraping contact, or fuzz button interconnect.

29. The method of claim 27, further comprising electrically coupling the at least one filter array conductive pathway to electronics within a housing of an electronics device.

30. The method of claim 27, wherein the at least one electrically conductive member comprises at least one solder joint, wherein the electrically coupling of the at least one filter array conductive pathway to the at least one feedthrough conductive pathway via the electrically conductive member comprises forming at least one solder joint between the at least one feedthrough conductive pathway of the feedthrough and the at least one filter array conductive pathway of the capacitive filter array.

31. The method of claim 30, wherein the at least one solder joint comprises at least one of an indium-silver alloy, a tin-silver alloy, tin-copper alloy, tin-silver-copper alloy, tin-lead alloy, and gold-tin alloy.

32. The method of claim 30, wherein forming the at least one solder joint comprises:
positioning a solder preform between the at least one feedthrough conductive pathway and the corresponding at least one filter array conductive pathway;
melting the solder preform to form the at least one solder joint between the at least one feedthrough conductive pathway and the corresponding at least one filter array conductive pathway.

33. The method of claim 27, wherein:
the feedthrough comprises a feedthrough substrate with the at least one feedthrough conductive pathway extending through the feedthrough substrate; and
the capacitive filter array comprises a capacitive filter substrate with the at least one filter array conductive pathway extending between a first filter substrate side and a second filter substrate side, and at least one capacitor filter of the capacitive filter array substantially surrounding at least a portion of the at least one filter array conductive pathway.

34. The method of claim 27, further comprising mounting the feedthrough within an opening in a ferrule.

35. The method of claim 34, further comprising forming a hermetic seal between the feedthrough and the ferrule.

36. The method of claim 34, further comprising mounting the ferrule within a housing of an electronics device.

37. The method of claim 36, further comprising forming a second hermetic seal between the ferrule and the housing.

38. The method of claim 27, further comprising grounding the capacitive filter array.

39. The method of claim 27, further comprising electrically coupling the at least one feedthrough conductive pathway to a corresponding conductor for an implantable medical device.

* * * * *